(12) United States Patent
Tang et al.

(10) Patent No.: US 10,549,064 B2
(45) Date of Patent: Feb. 4, 2020

(54) HUMIDIFIER AND LAYERED HEATING ELEMENT

(71) Applicant: ResMed Pty Ltd, Bella Vista, New South Wales (AU)

(72) Inventors: Zhuo Ran Tang, Sydney (AU); Ronald James Huby, Sydney (AU); Hargopal Verma, Sydney (AU); Andrew Roderick Bath, Sydney (AU); Roger Mervyn Lloyd Foote, Sydney (AU)

(73) Assignee: ResMed PTY LTD, Bella Vista, New South Wales (AU)

( * ) Notice: Subject to any disclaimer, the term of this patent is extended or adjusted under 35 U.S.C. 154(b) by 77 days.

(21) Appl. No.: 15/816,688

(22) Filed: Nov. 17, 2017

(65) Prior Publication Data
US 2018/0071480 A1    Mar. 15, 2018

Related U.S. Application Data

(63) Continuation of application No. 14/126,687, filed as application No. PCT/AU2012/000693 on Jun. 15, 2012, now Pat. No. 9,821,135.
(Continued)

(30) Foreign Application Priority Data

Jun. 16, 2011    (AU) .................................. 2011902350

(51) Int. Cl.
*A61M 16/16* (2006.01)
*B01F 3/04* (2006.01)
(Continued)

(52) U.S. Cl.
CPC .......... *A61M 16/16* (2013.01); *A61M 16/109* (2014.02); *A61M 16/1075* (2013.01);
(Continued)

(58) Field of Classification Search
CPC ................ A61M 16/16; A61M 16/109; A61M 16/1075; B01F 3/04
(Continued)

(56) References Cited

U.S. PATENT DOCUMENTS

| 4,719,335 A | 1/1988 | Batliwalla et al. |
| 4,967,057 A | 10/1990 | Bayless et al. |

(Continued)

FOREIGN PATENT DOCUMENTS

| CN | 200976685 Y | 11/2007 |
| CN | 101690385 A | 3/2010 |

(Continued)

OTHER PUBLICATIONS

A First Office Action dated Oct. 31, 2017 in a corresponding Japanese Patent Application No. 2016-231070 (5 pages), and an English translation thereof (8 pages).
(Continued)

*Primary Examiner* — Robert A Hopkins
(74) *Attorney, Agent, or Firm* — Nixon & Vanderhye P.C.

(57) ABSTRACT

A heating apparatus includes a heating element which converts electrical power to heat energy, a heatable element having a first surface and a second surface, and a dielectric laminate layer between the heating element and the first surface of the heatable element, wherein the dielectric laminate layer is thermally conductive to transfer heat energy from the heating element to the heatable element, and wherein the second surface of the heatable element is configured heat a liquid in a container.

17 Claims, 15 Drawing Sheets

Related U.S. Application Data

(60) Provisional application No. 61/628,622, filed on Nov. 3, 2011.

(51) Int. Cl.
*A61M 16/10* (2006.01)
*H05B 3/28* (2006.01)

(52) U.S. Cl.
CPC ............... *B01F 3/04* (2013.01); *H05B 3/28* (2013.01); *A61M 2205/3368* (2013.01); *A61M 2205/3653* (2013.01); *H05B 2203/002* (2013.01); *H05B 2203/013* (2013.01)

(58) Field of Classification Search
USPC ..................................... 261/142; 128/202.22
See application file for complete search history.

(56) References Cited

U.S. PATENT DOCUMENTS

| | | | |
|---|---|---|---|
| 5,451,747 | A | 9/1995 | Sullivan et al. |
| 8,049,143 | B2 * | 11/2011 | Andel ............... A61M 16/1075 128/203.12 |
| 2001/0014373 | A1 | 8/2001 | Lin et al. |
| 2003/0063931 | A1 | 4/2003 | Sanpei et al. |
| 2003/0141583 | A1 | 7/2003 | Yang |
| 2005/0175385 | A1 | 8/2005 | Cho et al. |
| 2009/0000620 | A1 | 1/2009 | Virr |
| 2009/0107980 | A1 | 4/2009 | Andel et al. |
| 2009/0218333 | A1 | 9/2009 | Kaastra |
| 2010/0147299 | A1 | 6/2010 | Row et al. |
| 2011/0023874 | A1 | 2/2011 | Bath et al. |
| 2011/0127249 | A1 | 6/2011 | Tenias |

FOREIGN PATENT DOCUMENTS

| | | |
|---|---|---|
| CN | 101772985 A | 7/2010 |
| CN | 101843181 A | 9/2010 |
| GB | 2 059 155 | 4/1981 |
| GB | 2 153 190 | 8/1985 |
| JP | 11-514792 | 12/1999 |
| JP | 2001-023759 | 1/2001 |
| JP | 2002-526901 | 8/2002 |
| JP | 2003-107946 | 4/2003 |
| JP | 2005-142523 | 6/2005 |
| JP | 2006-271953 | 10/2006 |
| JP | 2008-505435 | 2/2008 |
| JP | 2010/529400 | 8/2010 |
| WO | WO 2000/019773 | 4/2000 |
| WO | WO 2005/074322 | 8/2005 |
| WO | WO 2007/008075 | 1/2007 |
| WO | 2008/150172 | 12/2008 |
| WO | WO 2008/148154 | 12/2008 |
| WO | WO 2010/008279 | 1/2010 |
| WO | WO 2010/031126 | 3/2010 |

OTHER PUBLICATIONS

An Office Action dated Nov. 15, 2017, in a corresponding European Patent Application No. 12 800 518.8 (9 pages).
A Further Examination Report issued in corresponding New Zealand Application No. 738579 dated Sep. 24, 2018, (2 pages).
First Examination Report dated Jul. 24, 2014 in corresponding New Zealand Application No. 618941.
Extended European Search Report dated Nov. 7, 2014 issued in corresponding European Application No. 12800518.8 (9 pages).
Patent Examination Report No. 1 dated Mar. 21 2015, issued in corresponding Australian Patent Application No. 2012269735 (4 pages).
First Office Action dated May 21, 2015 in a corresponding Chinese Application No. 2015051801218560 (5 pages).
First Examination Report dated Sep. 1, 2015 in a corresponding New Zealand Application No. 710939 (2 pages).
Further Examination Report dated Sep. 18, 2015 in a corresponding New Zealand Application No. 618941 (2 pages).
Patent Examination Report No. 2 dated Jan. 12, 2016 in a corresponding Australian Application No. 2012269735 (5 pages).
Communication Pursuant to Article 94(3) EPC dated Mar. 14, 2016, in a corresponding European Application No. 12 800 518.8-1662 (6 pages).
Second Office Action dated Jan. 25, 2016 in a corresponding Chinese Application No. 201280040120.3 (13 pages), and English translation thereof (14 pages).
First Office Action dated Mar. 28, 2016 in a corresponding Japanese Application No. 2014-515004 (7 pages) and English translation thereof (7 pages).
First Examination Report dated Sep. 8, 2016, in a corresponding New Zealand Application No. 723636 (2 pages).
Notice of Allowance dated Oct. 31, 2016 in a correspondence Japanese Application No. 2014-515004 (3 pages).
International Search Report for PCT/AU2012/000693, dated Oct. 23, 2012.
Written Opinion for PCT/AU2012/000693, dated Oct. 23, 2012.
ElectroScience Thick-Film Materials & Ceramic Tapes, http://www.electroscience.com/heaterappnotes.html, 4 pages, printed Jun. 13, 2012.
High Power LEDs on Metal Core PCB, http://www.thorlabs.hk/NewGroupPage9.cfm?objectgroup_id=6071, 2 pages, printed Jun. 13, 2012.
Backer Heating Technologies, http://www.backerhti.com/flexible-heater/ptc-heater, 1 page, printed Jun. 13, 2012.
Yung, "Using Metal Core Printed Circuit Board (MCPCB) as a Solution for Thermal Management," Journal of the HKPCA, Issue No. 24, 2007, Q2, pp. 12-16.
JP Notice of Reasons for Rejection and English translation thereof dated Jun. 10, 2019 in corresponding JP Application P2018-139257 (13 pages).
CN First Office Action and English translation thereof dated Jun. 28, 2019 in corresponding CN application 201710536478.X (21 pages).

* cited by examiner

HUMIDIFIER AND LAYERED HEATING ELEMENT

CROSS-REFERENCE TO APPLICATIONS

This is a continuation of U.S. patent application Ser. No. 14/126,687, filed Dec. 16, 2013, which was the U.S. national phase of International Application No. PCT/AU2012/000693 filed Jun. 15, 2012 which designated the U.S. and claimed the benefit of Australian Provisional Application No. 2011902350, filed Jun. 16, 2011 and U.S. Provisional Application No. 61/628,622, filed Nov. 3, 2011. Each application mentioned above is hereby incorporated herein by reference in its entirety.

FIELD OF TECHNOLOGY

The present technology relates to electrical heaters and particularly to heaters used to heat fluids within containers. More particularly the present technology relates to electrical heaters used in humidification, such as humidification of breathable gases and to the devices including and methods of using such electrical heaters. The electrical heater may be used in a range of devices including in all forms of respiratory ventilation systems including invasive and non-invasive ventilation, Continuous Positive Airway Pressure (CPAP), Bi-Level therapy and treatment for sleep disordered breathing (SDB) conditions such as Obstructive Sleep Apnea (OSA), and for various other respiratory disorders and diseases.

BACKGROUND OF TECHNOLOGY

Respiratory apparatuses commonly have the ability to alter the humidity of the breathable gas to reduce drying of the patient's airway and consequent patient discomfort and associated complications. The use of a humidifier placed between the flow generator and the patient mask produces humidified gas that minimizes drying of the nasal mucosa and increases patient airway comfort. In cooler climates, warm air applied generally to the face area in and about the mask may be more comfortable than applying cold air.

Many humidifier types are available, including ones that are integrated with, or configured to be coupled to, the relevant respiratory apparatus. While passive non-heated humidifiers can provide some relief, heated humidifiers generally provide a higher humidity and temperature to the air increasing patient comfort. Heated humidifiers typically comprise a water tub having a capacity to hold several hundred milliliters of water, a heating assembly for heating the water in the tub, a control system to enable the level of humidification to be varied, a gas inlet to receive gas from the flow generator, and a gas outlet adapted to be connected to a patient conduit that delivers the humidified pressurized gas to the patient's mask.

Known heating assemblies may be suitable for its intended purpose, but require complex, costly, and manually intensive manufacturing processes. U.S. Pat. No. 6,660,977 describes an exemplary electrical heating plate structure.

SUMMARY OF TECHNOLOGY

One aspect of the present technology relates to a heated humidifier for use with respiratory therapy equipment.

Another aspect of the present technology relates to a heating apparatus or heating assembly for a respiratory therapy device, which comprises a heating element and a hot plate. The heating element and the hot plate are separated by a separation element which has a high thermal conductivity and high electrical insulation, e.g., low electrical conductivity. In an example, the separation element has a form, e.g., suitable substrate, which is suitable for printing onto the heating element. The hot plate may heat water in a container included in the respiratory therapy device.

Another aspect of the present technology relates to a heating apparatus for a respiratory therapy device which comprises a heating element and a hot plate spaced by a layer which electrically isolates the heating element and hot plate, and allows heat transfer between the heating element and the hot plate.

In an example, the heating apparatus includes a lamination of (i) a thermally conductive material, e.g., a hot plate, a metal plate, a thermally conductive substrate layer, (ii) a thermally conductive dielectric laminate layer, (iii) a heating element and (iv) a protective layer. The dielectric laminate layer provides electrical insulation between the heating element and hot plate to, for example, avoid electrical short circuits between the current flowing in the heating element and the hot plate. The heating element may be printed on or otherwise applied to the laminate layer by conventional printing techniques used in Printed Circuit Board (PCB) manufacture and assembly. Alternatively, the heating element may be applied as a sheet to the laminate layer and portions of the sheet etched away to form the tracks of the heating element. The heating element may be a narrow strip of conductive material, e.g., copper foil, arranged in a serpentine pattern. The thickness of the heating element and arrangement of the serpentine pattern may be selected based on the various design considerations, such as the shape of the bottom of the humidifier tub and the amount of heat energy to be transferred to the humidifier tub.

Another aspect of the present technology relates to a heating apparatus including a heating element which converts electrical power to heat energy, a heatable element having a first surface and a second surface, and a dielectric laminate layer between the heating element and the first surface of the heatable element, wherein the dielectric laminate layer is thermally conductive to transfer heat energy from the heating element to the heatable element, and wherein the second surface of the heatable element is configured heat a liquid in a container.

In an example, a protective layer may cover an outer surface of the heating element and an outer surface of the dielectric laminate layer. The protective layer may extend over peripheral edges of the heating element and dielectric laminate layer, and onto a peripheral portion of the first surface of the heatable element extending beyond the heating element and dielectric laminate layer.

In an example, the dielectric laminate layer may be a thin layer comprising at least one of polytetrafluoroethylene, e.g., Teflon®, polyimides, boron nitride, alumina, beryllium oxide, aluminum nitride, boron nitride, epoxy composite, and reinforced fiberglass. The thickness of the dielectric laminate layer may be in a range of about 20 µm to 160 µm, e.g., 60-120 µm. The dielectric substrate may be suitable to withstand a voltage above about 2 kV. The heatable element may include a conductive metallic plate, and the first and second surfaces are opposing surfaces of the plate. The heatable element may be a metallic printed circuit board (PCB) and the heating element may include tracks of conductive metallic foils arranged on the PCB.

In an example, the heating element may include conductive metallic foils, e.g., a copper foil, arranged in a serpentine pattern on the dielectric laminate layer. The heating element may have a direct current (DC) resistance in a range of about 5 to 25 Ohms, e.g., 5-15 Ohms, at room temperature. The thickness of each track of the heating element may be in a range, for example, of about 0.4 mm to 1 mm.

Another aspect of the present technology relates to a printed circuit board heater including a heating element track layer, a thermally conductive dielectric layer, and a substrate board having a first surface adapted to transfer heat into a container and a second surface, opposite to the first surface, on which the thermally conductive dielectric layer is sandwiched between the board and the track layer, wherein an electrical current terminal is provided to the track layer to allow the application of electrical energy to the heating element track layer which causes resistance heating of the track layer, and wherein heat energy from the track layer transfers through the thermally conductive dielectric layer to the substrate board which transfers the heat energy to the container. The substrate board may include a metal board or other printed circuit type board, forming for example a thermally conductive board.

Another aspect of the present technology relates to a method to form a heating apparatus including providing a metal plate having a first surface adapted to heat a liquid in a container, applying a thermally conductive dielectric layer to a second surface of the metal plate, wherein the second surface is opposite to the first surface, and applying a heating element layer to the thermally conductive dielectric layer such that the thermally conductive dielectric layer is sandwiched between the second surface of the metal plate and the heating element layer.

Another aspect of the present technology relates to a humidifier including a tub adapted to hold a volume of liquid and a heating apparatus including a PCB-type substrate. In an example, the substrate may include a metallic layer, a copper layer, and a dielectric laminate layer between the metallic layer and the copper layer. The metallic layer may be constructed of aluminum, stainless steel, other heat conductive metals, or even other types of PCB substrates. The dielectric laminate layer may be constructed of a ceramic or polymeric material. The heating tracks may be etched in the copper or heating alloy layer. A protective layer may be printed onto at least the copper layer.

In an example, the heating apparatus is provided to a humidifier chamber adapted to receive the tub. In another example, the heating apparatus is integral with the tub.

Another aspect of the present technology relates to a humidifier including a tub adapted to hold a liquid and a heating apparatus including a metallic hot plate, a heating element with copper, heating alloy or Positive Temperature Coefficient (PTC) heating tracks (e.g., heating tracks may be etched or otherwise provided in a layer of copper, heating alloy or PTC material, forming, for example, a PTC layer) or combinations thereof to provide heat to heat the liquid, a thermally conductive laminate layer constructed of, for example, a ceramic material, a polymeric material, or a ceramic and polymeric mixture material between the hot plate and the heating element, and a printed protective layer to cover at least the heating tracks.

Another aspect of the present technology relates to a humidifier including a tub adapted to hold a liquid and a heating apparatus including a thermally conductive hot plate, a heating element, a thermally conductive laminate layer between the hot plate and the heating element, and a protective layer to cover at least the heating element. The heating element may include copper or alloy or PTC heating tracks or combinations thereof to provide heat to heat the liquid.

Another aspect of the present technology relates to a humidifier including a tub adapted to hold a liquid and a heating apparatus including a thermally conductive hot plate, a heating element, a thermally conductive laminate layer between the hot plate and the heating element, and a protective layer to cover at least the heating element. The laminate layer is a dielectric laminate layer constructed of a ceramic or polymeric or polymeric mixture material.

Another aspect of the present technology relates to a humidifier including a tub adapted to hold a liquid and a heating apparatus including a thermally conductive hot plate, a heating element, a thermally conductive laminate layer between the hot plate and the heating element, and a protective layer to cover at least the heating element. The protective layer is printed or spread or molded onto at least the heating element.

Another aspect of the present technology relates to a process of making a heating apparatus for a humidifier including a tub to hold a liquid, including providing a substrate having a first side adapted to be in thermal contact with the liquid and a second side, etching heating tracks in the second side of the substrate, and applying a protective layer to the second side of the substrate to at least cover the heating tracks.

Another aspect of the present technology relates to a humidifier including a tub adapted to hold a liquid, a heating apparatus including a heating element having a first side and a second side, the heating element including heating tracks, a first thermally conductive laminate layer provided on the first side of the heating element, and a second thermally conductive laminate layer provided on the second side of the heating element.

Another aspect of the present technology relates to a humidifier including a tub having an inner portion adapted to hold a liquid, a heating apparatus including a thermally conductive hot plate and a heating element provided to a first side of the hot plate, and an overmold formed on the inner portion of the tub and completely surrounding the heating apparatus such that the heating apparatus is embedded within the overmold. The thermally conductive hot plate may be formed of a metallic material such as aluminum, stainless steel or other thermally conductive metals, or thermally conductive plastics.

Another aspect of the present technology relates a humidifier including a tub having an inner portion adapted to hold a liquid, a heating apparatus including a support substrate and a heating element provided to a first side of the support substrate, the support substrate being distal to the inner portion of the tub and the heating element being proximal to the inner portion of the tub, and a first thermally conductive protective layer provided to the heating element.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIG. 4-1 shows a schematic cross sectional view of a heating apparatus of the humidifier chamber shown in FIG. 3 according to an example of the present technology;

FIG. 4-2 shows a schematic cross sectional view of a heating apparatus of the humidifier chamber shown in FIG. 3 according to an example of the present technology;

FIG. 8-1 is a schematic view of a heating apparatus and electrical contact structure according to an example of the present technology;

FIG. 8-1A is an enlarged view of a portion of the heating apparatus and electrical contact structure shown in FIG. 8-1;

FIG. 9-1 is a schematic view of a heating apparatus and electrical contact structure according to an example of the present technology;

FIG. 9-2 is a schematic view of a heating apparatus and electrical contact structure according to an example of the present technology;

FIG. 12-1 is a schematic cross sectional view of a humidifier tub according to an example of the present technology;

FIG. 12-2 is a schematic cross sectional view of a humidifier tub according to an example of the present technology;

FIG. 15-1 is a schematic cross sectional view of a humidifier tub according to an example of the present technology;

FIG. 15-2 is a schematic cross sectional view of a humidifier tub according to an example of the present technology.

DETAILED DESCRIPTION OF ILLUSTRATED EXAMPLES

The following description is provided in relation to several examples (most of which are illustrated, some of which may not) which may share common characteristics and features. It is to be understood that one or more features of any one example may be combinable with one or more features of the other examples. In addition, any single feature or combination of features in any example or examples may constitute patentable subject matter.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

Respiratory Apparatus

Figure 1:
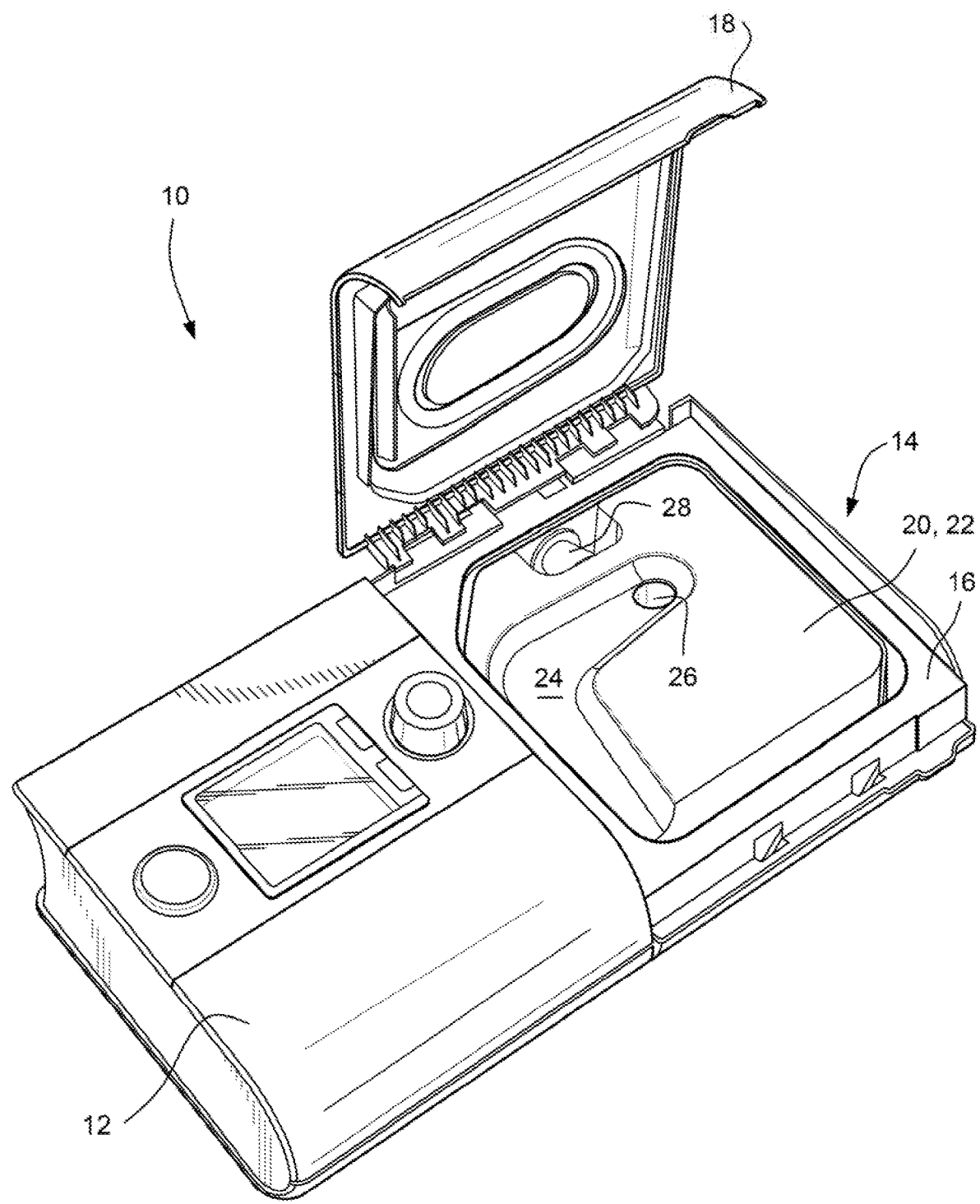
FIG. 1 shows a perspective view of a respiratory apparatus including a flow generator and a humidifier according to an example of the present technology.

FIG. 1 shows a respiratory apparatus 10 comprising a flow generator 12 and a humidifier 14. The humidifier 14 comprises a humidifier chamber 16 and a lid 18 for the chamber. The lid is movable, e.g., pivotable between open and closed positions. A water chamber, or humidifier tub 20, is seated or otherwise provided in the humidifier chamber 16 and covered by the lid 18, when the lid 18 is in the closed position. In another example, the humidification chamber may have a fixed lid rather than a movable/pivotable lid. In another example, the humidification chamber may have no lid.

The tub 20 is constructed and arranged to hold a liquid such as water which is used to add moisture to breathable gas. The tub 20 includes a tub lid 22 that is configured to direct a flow of breathable gas (airstream) generated by the flow generator 12 along a channel 24 and through an outlet 26 of the channel 24 that directs the gas into the tub 20. The tub 20 includes a gas outlet 28 for the humidified flow of breathable gas. The gas outlet 28 is connectable to a tube (not shown) configured to deliver the humidified gas flow to a patient interface, e.g. a mask. The tub may have different configurations, for example with inlets and/or outlets in different locations.

Figure 2A:
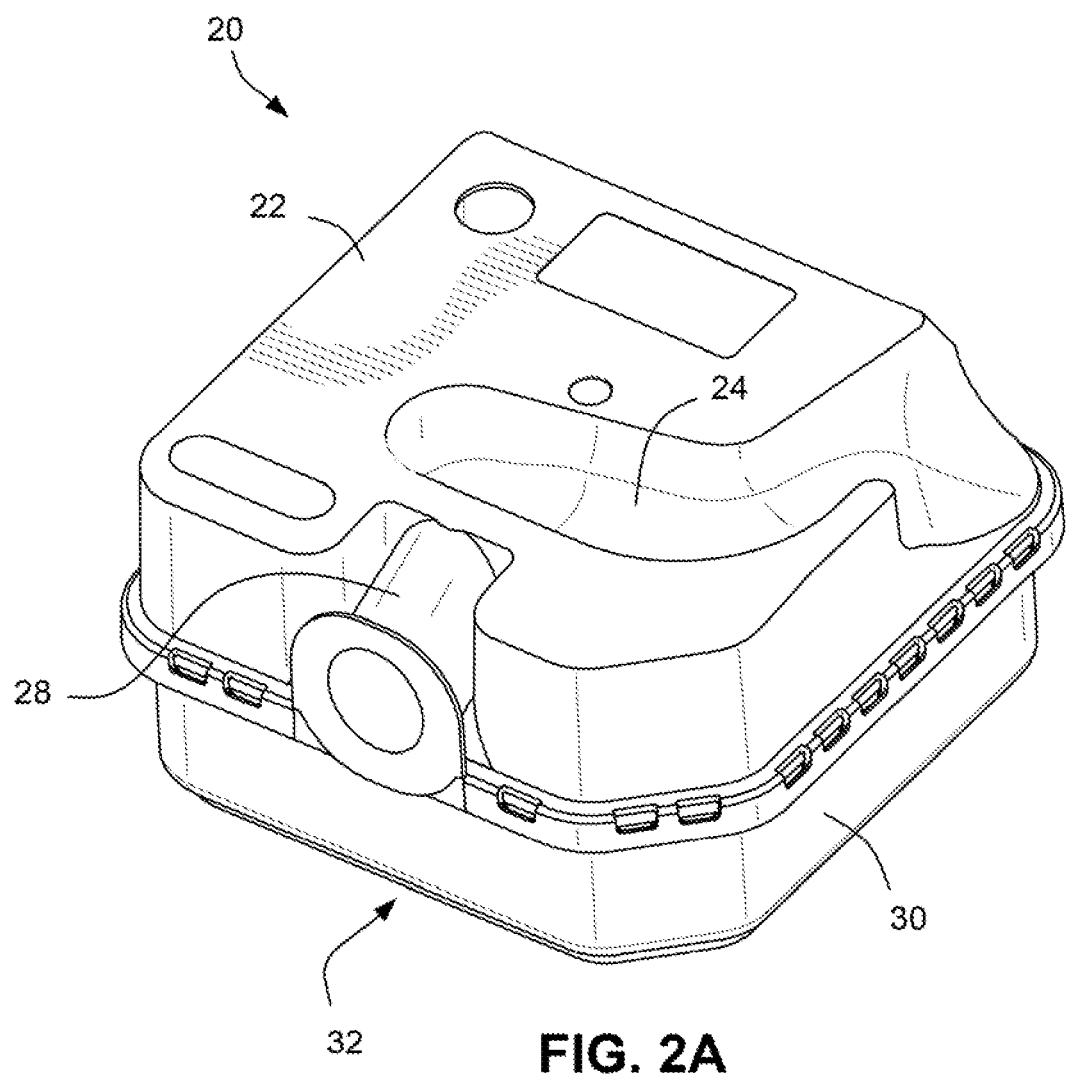
FIGS. 2A and 2B show upright and inverted perspective views of a humidifier tub of the humidifier shown in FIG. 1 according to an example of the present technology.
Figure 2B:
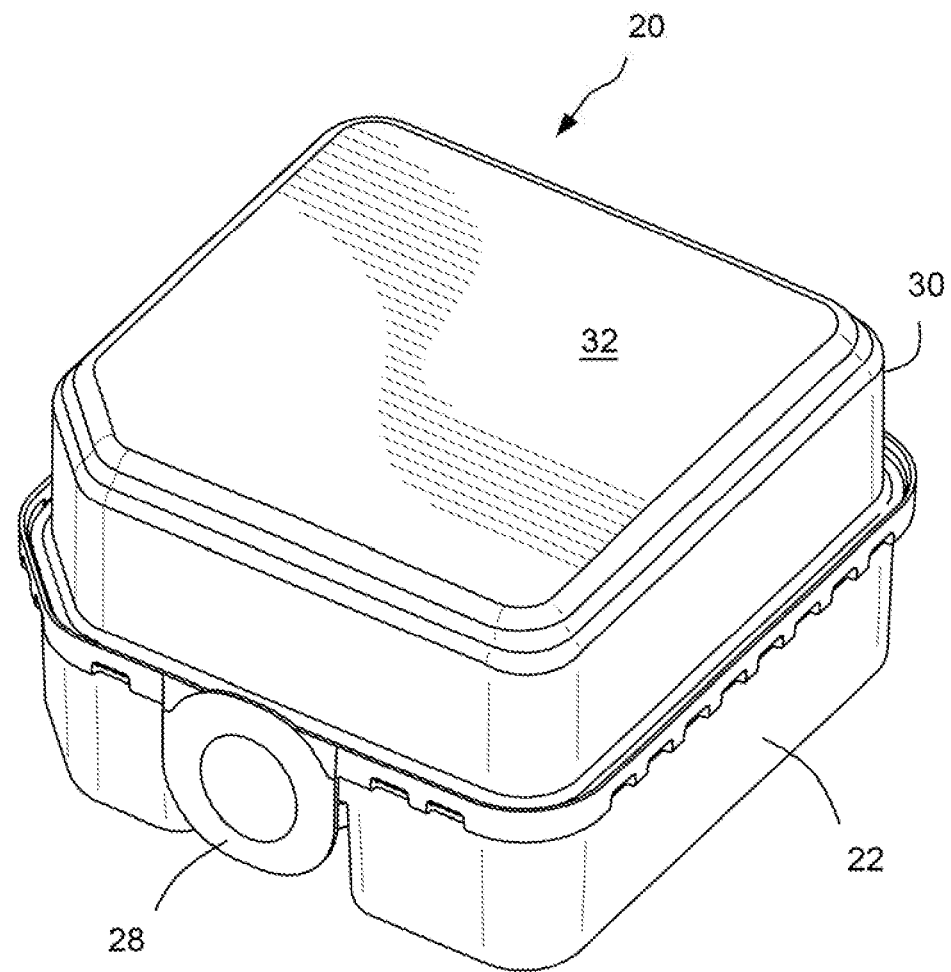
Figure 3:
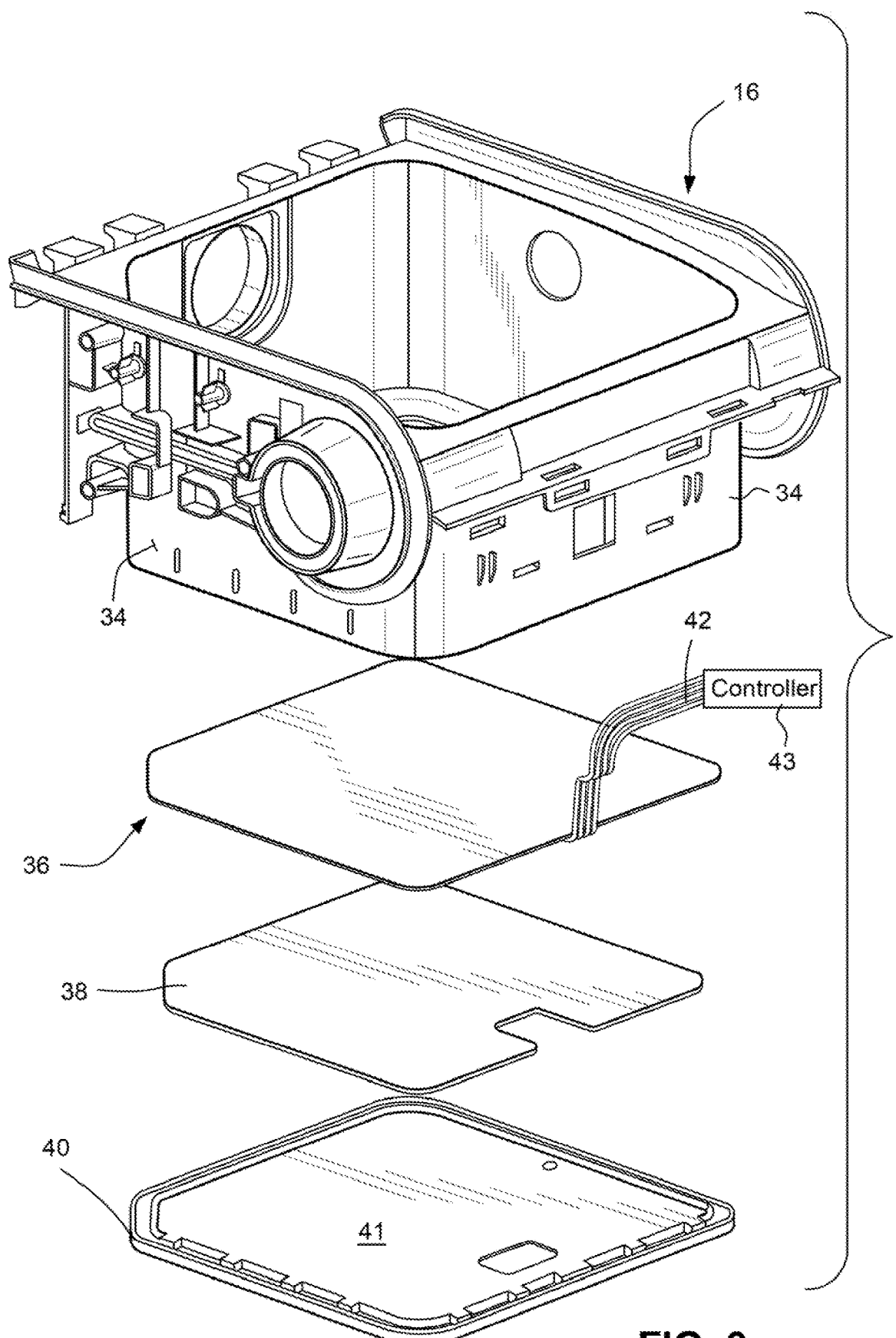
FIG. 3 shows an exploded assembly view of a humidifier chamber of the humidifier shown in FIG. 1 according to an example of the present technology.

FIGS. 2A and 2B show the exemplary humidifier tub 20 separated from the humidifier chamber 16. The tub may be removable from the humidifier chamber 16 to fill the tub with water or clean the tub. The lid 22 of the tub connects to a tub bottom or bottom container 30, wherein the lid 22 and tub bottom 30 fit together to form the tub 20. When the tub 20 is placed in the humidifier chamber 16, the tub bottom 30 is in thermal contact with a heating apparatus or heating assembly 36 of the humidifier chamber 16, shown in FIG. 3. The tub bottom 30 comprises a heat conductive material, e.g., a metal material such as aluminum, copper, brass, or stainless steel, or any other alloy or thermally conductive suitable material for conducting heat received from the heating apparatus 36 to the liquid contained inside the tub 20. In an example, the tub bottom is formed entirely of a metal. Alternatively, the tub bottom may have a bottom plate 32 formed of a heat conductive material while the remainder of the tub is formed of another material, e.g., a plastic material. Alternatively, the tub bottom and the heating apparatus may be integral, e.g., bottom plate and heating apparatus may be integral. That is, the heating apparatus may form the tub bottom and directly heat the liquid contained inside the tub. While the heating apparatus is shown in FIG. 3 as being planar and at the bottom of the chamber 16, the heating apparatus may have other forms and be at other positions with respect to the chamber and tub. In another example, the heating apparatus may be located in other regions, such as on a side wall of the tub and in direct contact with the liquid to be heated. In another example, the heating apparatus may be shaped to conform to the side wall 34 of the humidifier chamber 16 such that the heating apparatus abuts against a metal portion of a side wall of the tub. In another example, the heating apparatus may be provided within the tub and elevated from the tub bottom 30 such that water is provided over top and bottom surfaces of the heating apparatus. The design, shape and composition of the tub described herein is exemplary and other tubs and liquid containers may be suitable for the present technology.

As shown in FIG. 3, a cradle bottom 40 is provided beneath the heating apparatus 36 and an insulation layer 38 is provided between the heating apparatus 36 and the cradle bottom 40. The cradle bottom 40 may be a releasable bottom plate to the humidifier chamber 16. The cradle bottom 40 may include a flat surface 41 structured to form a seat for the insulation layer 38 and the heating apparatus 36. The insulation layer 38 may be separable from the cradle bottom and the heating apparatus, or bonded to the cradle bottom and/or heating apparatus. The insulation layer is structured to prevent excessive heat transfer to the cradle bottom 40 to avoid burning a person touching the bottom cradle or damaging furniture on which the humidifier chamber is seated. In an alternative example, the insulation layer 38 may not be provided, as heat transfer from the heating apparatus 36 to the tub bottom 30 may be substantially effective and heat dissipation towards the cradle bottom 40 may not be significant.

Electrical leads 42 are connected to the heating apparatus 36 to provide electrical power to the electrical components of the heating apparatus 36. The electrical leads 42 may extend to an electrical coupling within or external of the humidifier chamber 16. The electrical leads may connect the heating apparatus to a controller 43 which may be connectable to a power source, such as an electrical wall socket. The controller may regulate the voltage or current applied to the heating apparatus. In an example, the controller may provide one or more of the following: power switch, temperature sensing, fault detection (e.g., open, short, over temperature, poor connection, sensor, water ingress to PCB, CPU, power device, power switch), fault protection, and/or electrical interfacing to heater.

Heating Apparatus

Figures 1, 4:
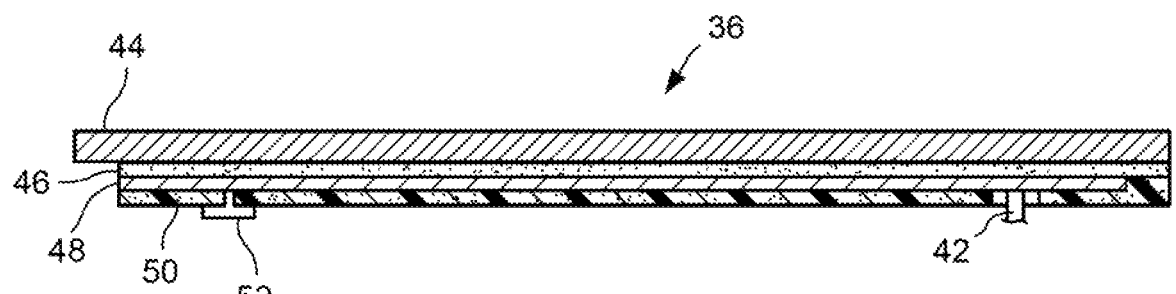
Figure 5:
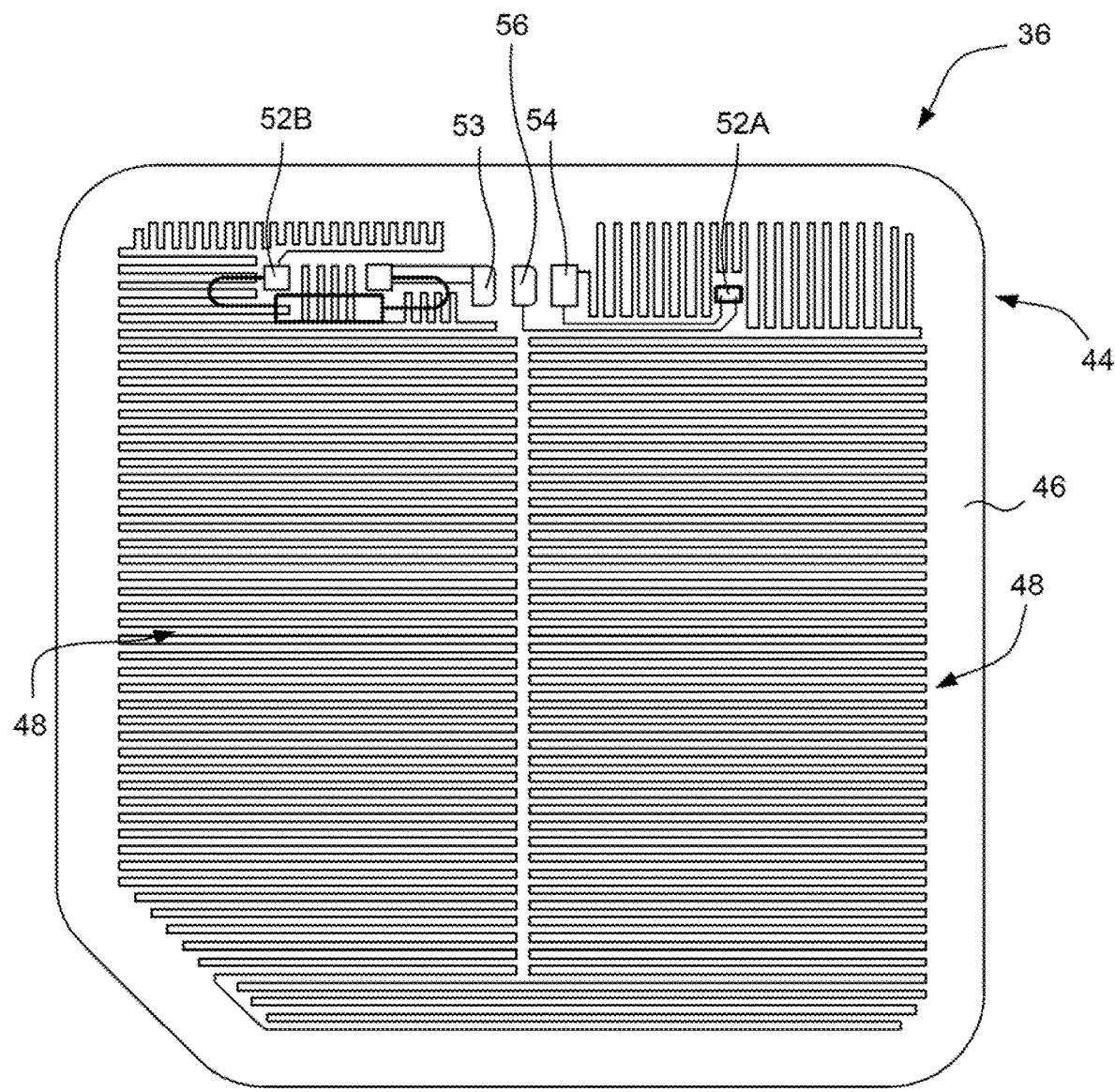
FIG. 5 shows a schematic view of a circuit layout of the heating apparatus shown in FIGS. 3 and 4-1 according to an example of the present technology.

FIGS. 4 and 5 show a heating apparatus or heating assembly 36 according to an example of the present technology. As illustrated, the heating apparatus 36 includes a hot plate 44 (also referred to as a heatable element, metal board, or substrate), a thermally conductive laminate layer 46, a heating element 48, a protective layer 50, at least one electrical component 52 (Temperature sensing and/or protection), and electrical leads 42 supplying electricity to the heating element 48 and the at least one electrical component 52.

As described below, the heating apparatus according to an example of the technology provides an assembly that is simpler to process, more efficient and reliable, and lower cost.

Hot Plate

The hot plate 44 comprises a heat conductive material such as aluminum (e.g., anodized aluminum), stainless steel, copper, or any other suitable metal or metal alloy, forming for example a metal alloy plate such as an aluminum plate, a stainless steel plate or a copper plate. The metallic hot plate may have a surface treatment such as being anodized to form a protective oxide layer which resists corrosion. The hot plate may be thin such as having a thickness in a range of about 0.6 to 1.6 mm, e.g., 1.0 to 1.5 mm. In an example, the hot plate may comprise a substantial portion of the total thickness of the heating apparatus. For example, the heating apparatus, which includes the hot plate, thermally conductive laminate layer, heating element and protective layer, is similarly thin and may have a thickness in a range of about 0.5 to 1.7 mm, e.g., 1.1 to 1.6 mm, wherein all but about 0.1 to 0.2 mm of the thickness of the heating apparatus is attributed to the hot plate. In an alternative example, the hot plate may be formed of other suitable materials such as a heat conductive non-metal material, such as a ceramic material and thermal conductive plastics.

Thermally Conductive Laminate Layer

The thermally conductive laminate layer 46 may be a coating, layer or board bonded to the hot plate. The thermally conductive laminate layer 46 comprises materials which have good thermal conductivity properties, but are low in electrical conductance, e.g., relatively high electrical resistance, and thus may be referred to as a dielectric laminate layer. The thermally conductive laminate layer may be a composite layer of dielectric particles embedded in a filler material, such as a resin. For example, the laminate layer 46 may include electrically insulating dielectric materials, such as ceramics, polymers, polymer and ceramic, polymer mixed with inorganic particles, ceramics coated with polytetrafluoroethylene, e.g., Teflon®, polyimides, boron nitride, alumina, beryllium oxide, aluminum nitride, boron nitride, epoxy composite, and reinforced fiberglass, arranged to form an electrical insulating layer. In an example, the dielectric breakdown voltage of the laminate layer may be above 2 kV. Further, the laminate layer 46 may be rigid or flexible, and may be planar or have some other shape which may conform to a bottom and/or side of the tub.

The thermally conductive laminate layer 46 provides electrical insulation between the heating element 48 and the hot plate 44. The thermally conductive laminate layer also is an efficient conductor of the heat generated by the heating element 48 and transfers the heat to the hot plate 44. Heat generated by the heating element 48 flows efficiently through the thermally conductive laminate layer and through the hot plate 44 to the tub and water contained in the tub. Heat generated by the heating element 48 is therefore drawn away or dissipated from the heating element 48 and transferred towards the hot plate 44. That is, the high thermal conductivities of the laminate layer 46 and hot plate 44 provide an effective thermal conductive gradient that allows heat to efficiently flow from the heating element 48, through the laminate layer 46, the hot plate 44 and to the tub 20. The hot plate 44 functions as a heat sink that draws heat energy generated in the heating element 48 and distributes the energy to heat the water in the tub. Heat is collected and accumulated at the hot plate 44 for use in heating the tub bottom 30. The heat conductive tub bottom 30, which is in thermal contact with the hot plate 44, receives the heat and uses it to heat the liquid contained inside the tub 20, thereby adding humidity to the pressurized gas (e.g., 4-20 cmH$_2$O) that passes through the tub.

In an example, the laminate layer 46 has a dielectric thermal conductivity in a range of 0.5 to 4 watts per meter Kelvin (W/m·k), e.g., in a range of about 0.5 to 1.00 or greater. The laminate layer may be a thin layer, e.g., 20 micrometer (μm) to 160 μm, e.g., 60-120 μm. The thinness of the laminate layer contributes to the minimal resistance to thermal transmission through the laminate layer.

Figures 2, 4:
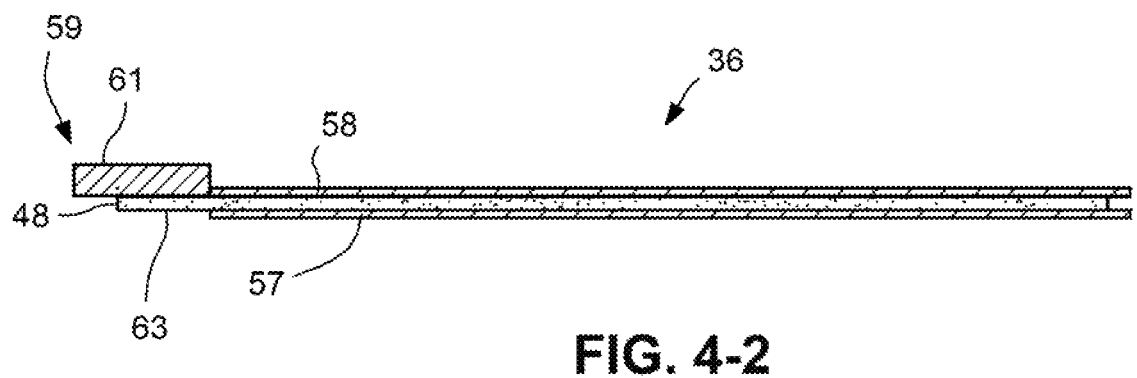

In an example, the heating apparatus may not include a separate hot plate 44. Rather, the thermally conductive laminate layer 46 itself may form the heating surface. This configuration may provide a flexible circuit arrangement. In an example, the heating element 48 may be disposed between two layers 57, 58 of thermally conductive laminate material (e.g., flexible polyimide film such as Kapton™), as shown in FIG. 4-2. One or more thermal conductive substrates, pads, pins or contacts 61, such as a metal substrate, pad, contact or pin (e.g., made from aluminum, stainless steel, copper, etc.) may be bonded to a portion (e.g., an edge portion) of the heating element 48 to form a connector section 59. An exposed portion of the heating element 48 adjacent the substrate 61 may form an electrical contact 63 to receive electrical power. The connector section 59 may be formed prior to forming an additional overmolded protective layer (such as described below) on top of the heating element 48. The arrangement of the connector section 59 provides a procession connector which allows direct electrical and/or thermal contact with the heating element 48 such that additional functions (e.g., thermal sensing of the heating element) may be performed.

Heating Element

The heating element 48 may be formed of electrical resistance heating materials such as copper, electrical heating alloys such as Iron-Nickel, Copper-Nickel, Iron-Chromium-Aluminum, Nickel-Chromium, as well as other materials such as PTC ink materials, Carbon ink materials, copper foil, and other materials having a relatively low electrical resistance or combinations thereof. The heating element 48 may comprises metallic foils, tracks or strips arranged in a serpentine pattern, such as in rows (e.g., see FIG. 5). It is noted that each line of the heating element 48 in FIG. 5 represents a "track." The heating element 48 may be printed or applied to the thermally conductive laminate layer 46, as is shown in FIG. 5. The layout of the heating element and the shape of the serpentine pattern may depend on the shape of the bottom plate 32 of the tub. In use, the heating element converts electrical power to heat energy.

In an example, the tracks of the heating element 48 may be evenly distributed across the laminate layer to provide an even heating profile to the hot plate 44. For a target heating performance, the track design of the heating element depends on a number of factors. For example, the resistivity of the heating element material affects the track layout design and the track coverage of the laminate layer 46 and the hot plate 44. In another example, a heating alloy is a better electrical resistance heater material as compared to copper. Therefore, to achieve a similar heating profile, copper heating tracks may be thinner in width (e.g., in a range of about 0.3 mm to 2 mm, e.g., 0.4 to 1 mm) and longer in length as compared to heating alloy or aluminum heating tracks. In such configurations, more area of the heating apparatus may be covered to achieve a similar desired heating profile. A person skilled in the art would understand that other track configurations may be provided to produce different heating profiles.

Figure 7:
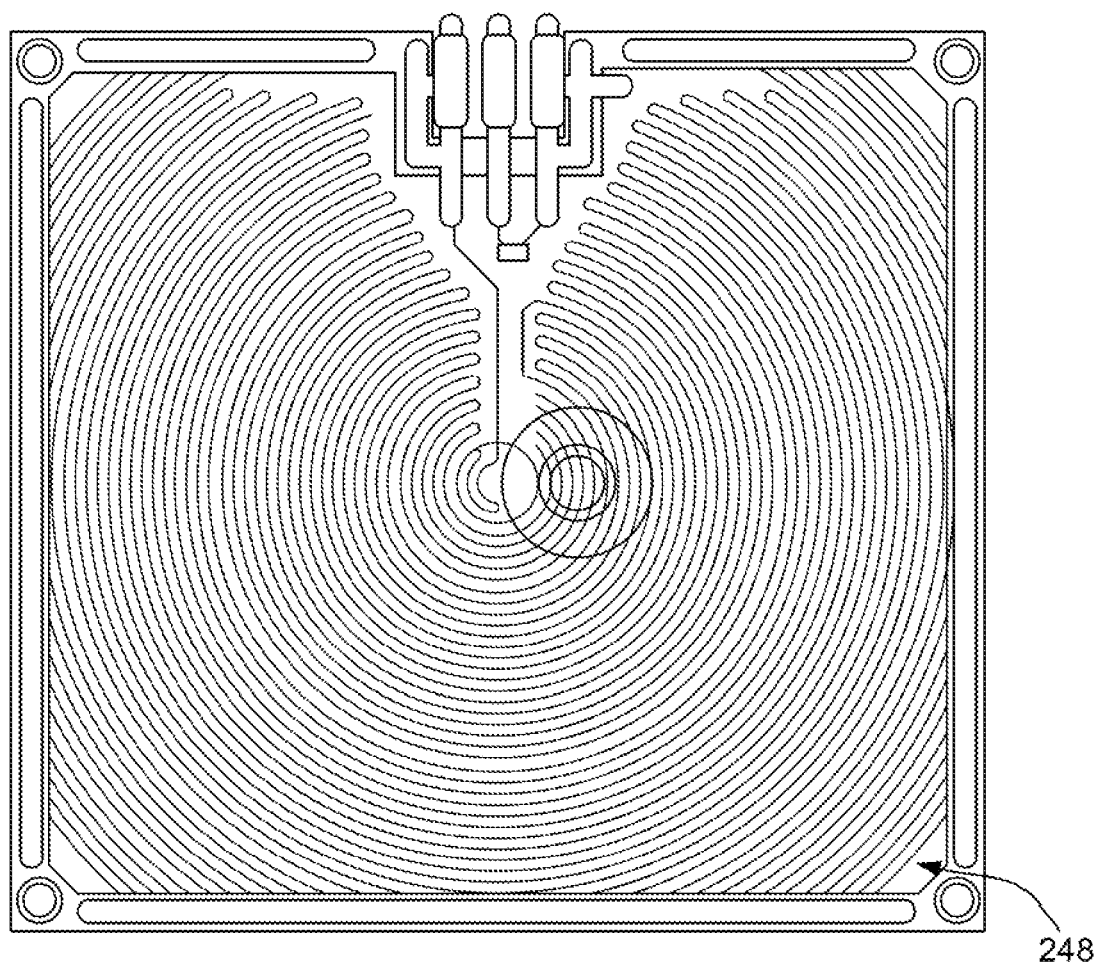
FIG. 7 shows a schematic view of a circuit layout of a heating apparatus according to an example of the present technology.

FIG. 7 shows a heating element 248 including an alternative example of the track layout or pattern. As illustrated, the tracks or strips are arranged in a concentric ring-like manner. Advantages of this layout include improved thermal distribution as well as improved tolerance for thermal expansion/contraction of the tracks as it heats/cools. This layout also improves the resistance accuracy during the heating process.

Protective Layer

The protective layer 50 may comprise materials commonly used for 'solder masks,' for example polymer or acrylic. Solder masks are conventionally printed on or otherwise applied to coat a printed circuit board (PCB), thermally conductive laminate layer and conductive traces of the heating element during PCB and metal core printed circuit board (MCPCB) manufacturing processes. In the context of the heating apparatus, the protective layer may be printed on or otherwise applied to coat the heating element 48 and the thermally conductive laminate layer 46. The heating element is sandwiched between the protective layer 50 and the thermally conductive laminate layer 46. The protective layer 50 may extend over the peripheral edges of the heating element 48 and directly coat portions of the thermally conductive laminate layer 46, e.g., see right edge of apparatus shown in FIG. 4-1.

Exemplary materials for the protective layer 50 include, for example, screen printable epoxy mask, liquid photoimageable solder mask (IPSM) and dry film photoimageable solder mask (DFSM). The protective layer 50 seals the heating apparatus 36 to prevent current leakage, as well as to protect the laminate layer 46 and the heating element 48 against environmental factors such as corrosion and physical scratching. The protective layer 50 may be printed on or otherwise applied to directly coat the surfaces of the hot plate 44 not covered by the laminate layer. The protective layer 50 may also provide electrical insulation and some thermal insulation between the heating element 48 and the insulating layer 38 in the cradle bottom 40 of the humidifier chamber 16.

The protective layer 50, such as a solder mask, may be applied over the laminate layer 46 and the heating element 48 by screen printing, well known mask printing techniques or as a sheet bonded with adhesives to the heating element and laminate layer. Further, stencils may be positioned over certain locations on the heating element and laminate layer so that the contact pads and possibly other locations are not coated by the protective layer. After the protective layer is printed, applied or otherwise bonded to the heating element and laminate layer, the stencil may be removed to expose the contact pads and other locations which are to be exposed.

Contact pads and/or other conductive portions of the heating element may be exposed through the protective layer 50 to allow for connection of the electrical leads to the heating element, e.g., by surface mounting technology. These openings in the protective layer for the contact pads may be automatically applied during an automated printing or coating process.

Electrical Leads

The electrical leads 42 provide a conductive path for power from an electrical power source to be applied to the heating element 48. The electrical leads may be coupled to electrical wires that fit into a power source, such as a transformer or inverter or into an electrical power wall-socket via appropriate isolation. When electrical power is applied through the electrical leads 42, heat is generated by electrical resistance heating of the heating element 48. The heat generated by the heating element 48 is transferred through the thermally conductive laminate layer 46, the hot plate 44 and to the bottom plate 32 of the humidifier tub 20 to heat the water therein.

Contact Pads

The heating element may include conductive or contact pads 53, 54, printed or placed on the laminate layer 46. The conductive pads provide an electrical connection point for the electrical leads 42, e.g., conductive pad 53 providing a positive power terminal and conductive pad 54 providing a negative power terminal. Electrical power flows from a power source, through the leads, the power terminals and the heating element 48. Additional contact pads may be used to provide electrical connections to other electrical device(s) or contacts (e.g., spring contact or spring contacts) on the laminate layer 46. For example, as shown in FIG. 5, the electrical components 52 noted with respect to FIG. 4-1 may include a thermo sensor 52A and a thermo fuse 52B which are connected to tracks of the heating element 48. The electrical connection provided by contact pad 56 (e.g., a thermo sensor positive terminal) may be between the thermo sensor 52A and another source of electrical power provided by a different set of leads for separately providing power to the thermo sensor 52A. Another source of electrical power may be provided if the power requirements of the other electrical device(s), e.g., thermo sensor 52A, differ from the power requirements for the heating element. The thermo fuse 52B may be mounted on top of the solder mask and connected to the contact pads which are in electrical contact with the heating element. The thermo fuse stops current flow through the heating element if the heat becomes excessive. The electrical connections between the contact pads and the electrical leads or sensor wires may be made by soldering or any other known electrical connection processes, for example automated surface mounting technologies.

In an example, a nominal voltage source of between 12 Volts (V) and 36V (such as between 8V and 40V) provides power to the heating element 48. Other voltages may be used in accordance with suitable operational parameters of the heating element 48. The heating element 48 may substantially cover the entire area of the laminate layer, while allowing a margin for clamping in a coating treatment process to apply the printed protective layer 50 (e.g., applying a solder mask).

Assembly

The heating apparatus 36 may be formed using known printed circuit board (PCB) manufacturing techniques for making metal PCBs, such as metal core printed circuit board (MCPCB) techniques. These techniques are highly automated and are adapted to apply conductive tracks on metal PCBs. In MCPCBs, metal plates serve both as a printed circuit board base and a heat sink for electronic components mounted to the plate. Heat from the electronic components is dissipated by the metal plate to avoid overheating of the electronic components. The metal plate may be formed of any appropriate heat conducting metal, for example aluminum (aluminium), stainless steel, or other heat conducting metals, or heat conducting polymers or plastics.

For example, the heating element 48 may be applied to the thermally conductive laminate layer 46 using MCPCB manufacturing techniques for making metal PCBs. The heating element may be applied by printing the conductive tracks on the laminate layer 46. The heating element may also be formed by applying a conductive sheet to the laminate layer, applying a mask to the sheet shaped as a mirror image of the desired pattern of the heating element and etching away the portions of the conductive sheet not covered by the mask. The heating element 48 may also be formed on the laminate layer 46 by vacuum deposition techniques. Further, the serpentine pattern of the heating element may be selected based on the shape of the bottom of the water tub and the amount of heat energy to be delivered to the tub.

In another example, a PCB including a metal layer, a dielectric layer, and a copper layer may be selected based on size/performance characteristic requirements. Copper heating tracks are created in the copper layer according to track specification, e.g., by etching. A printed protective layer (e.g., solder mask) is applied to cover the heating tracks. The tracks/printed protective layer may accommodate for electrical connection points for surface mounting (or solder) electrical components (e.g., thermo fuse, thermo sensor).

The assembly process disclosed herein for the heating apparatus may be fully or nearly fully automated, which allows for the production of heating apparatuses having high quality and uniform consistency. The assembly process disclosed herein may also result in reduced assembly costs and reduced repair or replacement costs for the heating element due to the automation. In addition, such PCB technique uses advanced heat transfer structure, material and technology, provides much simpler structure, provides excellent thermal performance, involves much less safety concerns, provides easy quality control and high yield, and/or provides easy mass production capacity increase and multiple supply.

FIG. 5 shows an example of the heating apparatus 36 formed by metal printed circuit board printing and manufacturing processes. FIG. 5 shows the heating element 48 arranged in rows on the thermally conductive laminate layer 46. The laminate layer 46 may be coincident or coextensive with the hot plate 44 (e.g., as shown in FIG. 5 which shows the hot plate 44 below the laminate layer 46), or the perimeter of the hot plate 44 may extend slightly beyond the perimeter of the laminate layer 46 (e.g., as shown in FIG. 4-1).

In FIGS. 3 to 5 described above, the heating apparatus is provided as a separate and distinct structure from the humidifier tub which is adapted to contact the tub to heat liquid contained inside the tub. Alternatively, the heating apparatus may be integral with the tub and form the tub bottom so as to directly heat liquid contained inside the tub. Examples of such direct heating apparatus are described below.

Figure 6:
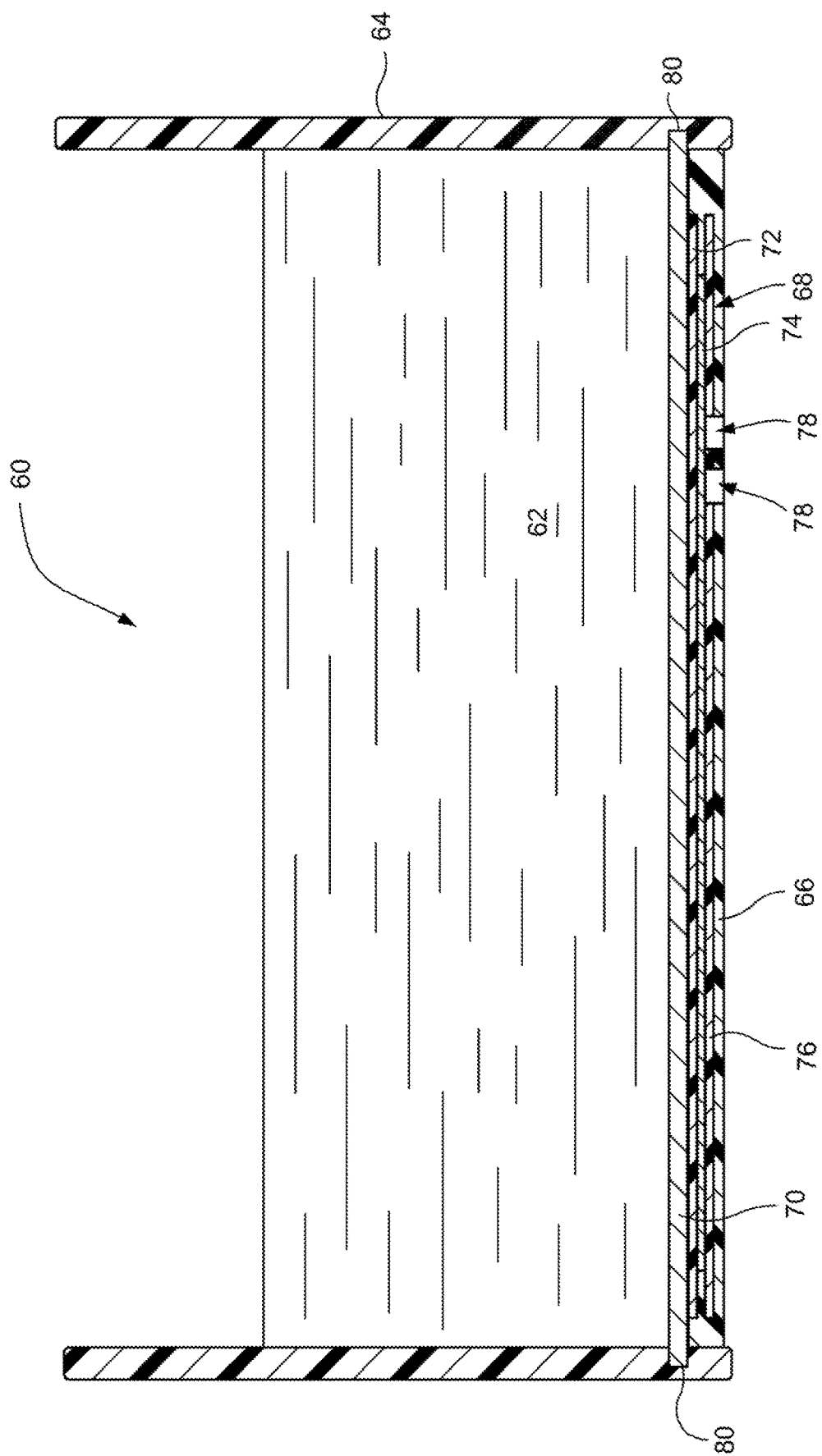
FIG. 6 is a schematic cross sectional view of a humidifier tub including a heating apparatus according to an example of the present technology.

FIG. 6 shows a humidifier tub or water tub 60 for heating water 62 according to an example of the present technology. The tub may be suitable for seating in a humidifier chamber or may be provided as a stand-alone device. The tub 60 includes sidewalls 64, or sidewall portions, or tub sidewalls extending around the entire perimeter of the tub and a bottom wall 66 which joins to the sidewalls. A heating apparatus or heating assembly 68 is incorporated into the bottom wall 66. In an example, the sidewalls 64 and bottom wall 66 (e.g., formed of plastic) are overmolded onto the heating apparatus 68. In the illustrated example, the bottom wall 66 is molded over peripheral edges of the dielectric layer 72, heating element 74, and protective layer 76. In an alternative example, as described above, the protective layer may cover one or more layers of the heating apparatus.

The heating apparatus 68 is formed as a lamination of a hot plate 70, a thermally conductive dielectric layer 72, a heating element 74 and a protective layer 76. The hot plate may be a metal plate having a first side with an anodized coating which is adapted to form the bottom interior surface of the tub exposed to the water 62. The opposite side of the hot plate receives the thermally conductive dielectric layer 72 which may be a resin with dielectric particles, as is described above.

Figure 13:
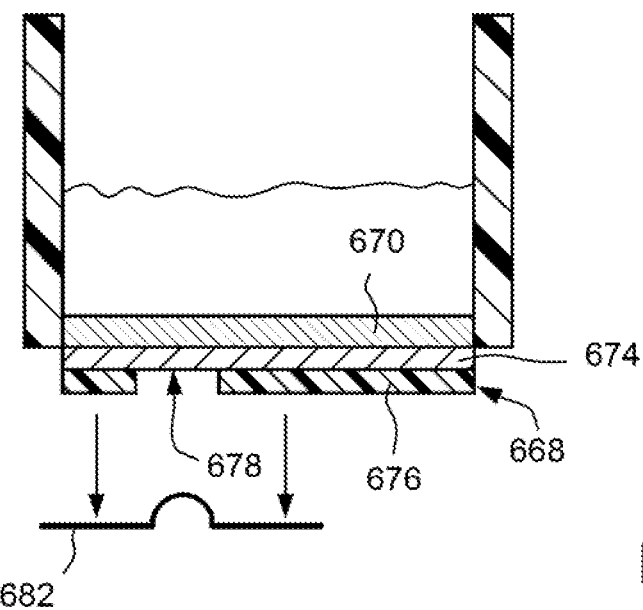
FIG. 13 is a schematic cross sectional view of a humidifier tub including a heating apparatus according to an example of the present technology.

The heating element 74 may be a serpentine track of a metallic foil, e.g. forming a serpentine track of conductive foil, that is printed on or otherwise applied to a side of the dielectric layer 72 opposite to the hot plate 70. Contact pads 78 may be arranged at each of the ends of the track of the heating element or close to the edge of the hot plate to allow for a spring electrical contact. The contact pads 78 may be exposed through the protective layer 76. Further the contact pads may be formed with raised terminals which protrude slightly from the bottom wall 66 of the tub. Such arrangement allows the contact pads 78 to engage power terminals at, for example, the bottom of a humidifier chamber which provides electrical power to the heating element. For example, FIG. 13 illustrates a direct-heating humidifier tub including a heating apparatus 668 that forms the bottom wall of the tub (e.g., heating apparatus provided to bottom of tub by overmolding or clip-in). FIG. 13 shows the hot plate 670, heating element 674 and protective layer 676 of the heating apparatus, with a contact pad 678 exposed through the protective layer 676. In use, the exposed contact pad 678 may engage a power terminal or spring electrical contact 682 at the bottom of a humidifier chamber when the tub is engaged with the humidifier chamber, e.g., push-down electrical contact connection configuration.

The edges 80 at the perimeter of the hot plate 70 may fit, e.g., snap, into grooves at the lower edge of the sidewalls 64. The edges 80 may extend beyond the edge of the protective layer 76, heating element 74 and dielectric layer 72. The joint between the edges 80 of the hot plate 70 and the sidewalls 64 may be sealed to secure the heating assembly to the sidewalls and to prevent water leakage from the tub. In an example, as noted above, the sidewalls 64 may be overmolded to the edges 80 of the hot plate 70.

Figure 11:
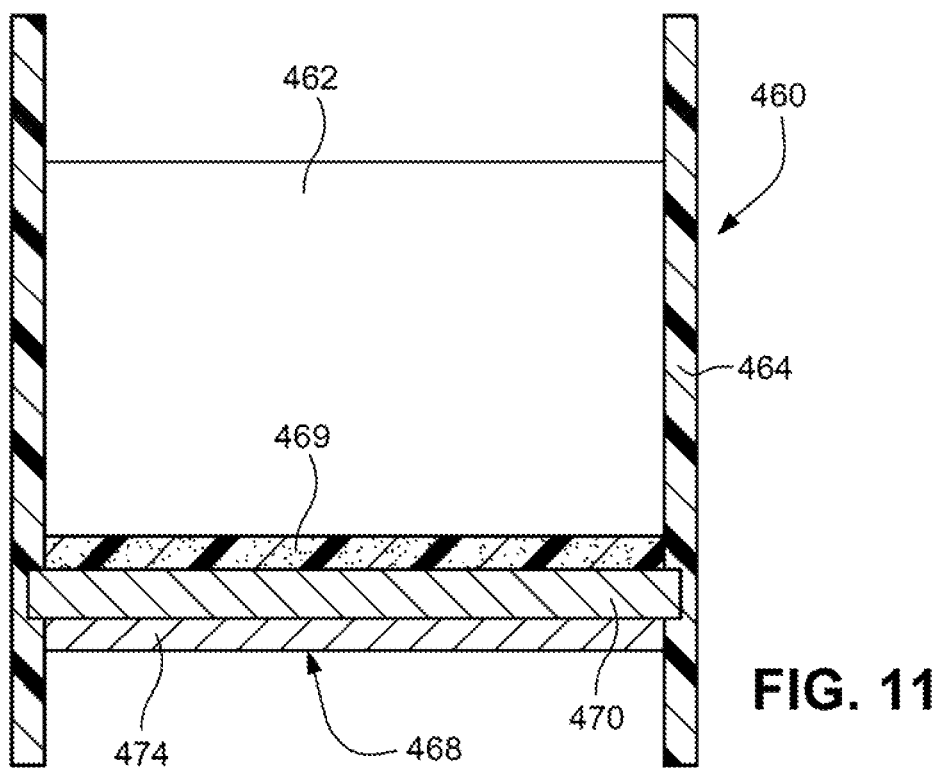
FIG. 11 is a schematic cross sectional view of a humidifier tub according to an example of the present technology.
Figures 1, 12:
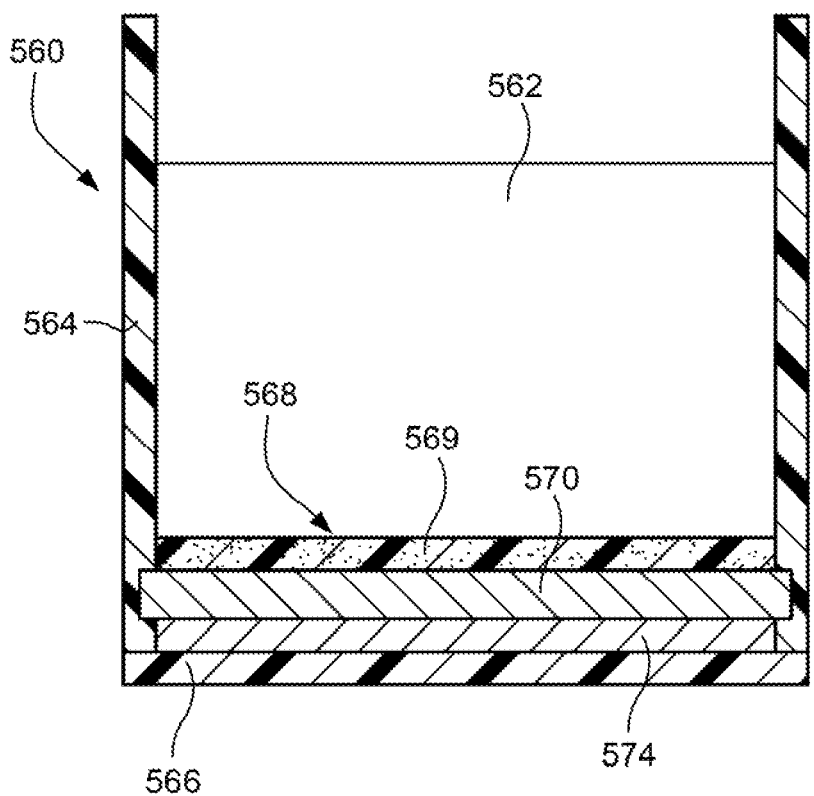
Figures 2, 12:
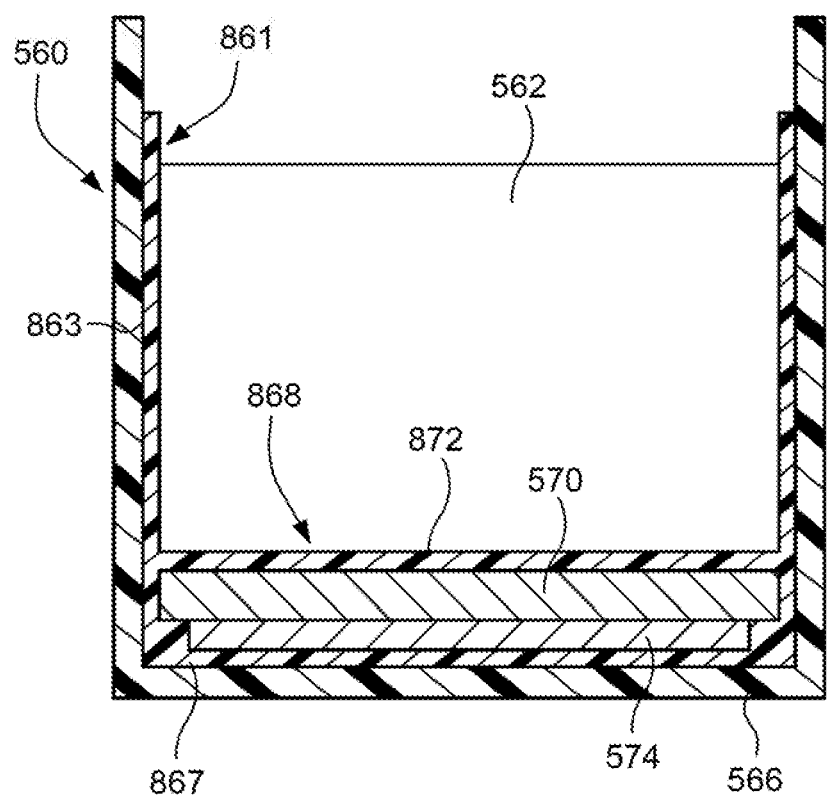

The heating assembly may include a protective coating 469, 569 provided over the hot plate, as shown in FIGS. 11 and 12. The protective coating may be overmolded over the hot plate to provide a water and/or vapor sealed protection layer across the heating surface. The protective coating is thermally conductive so as to effectively transfer heat from the hot plate to the water in the tub. Furthermore the protective coating is preferably formed of a bio-compatible material and may be formed of silicone, Teflon®, UV cured polymers or other thermally conductive plastic materials, such as CoolPoly™ products. The protective coating may also provide an easily cleanable surface.

Furthermore, the protective coating may allow the heater assembly to be inserted or located directly within the water tub body, which may provide enhanced thermal performance. The use of a protective over molded coating is further described in U.S. 61/611,137, filed 15 Mar. 2012, which is incorporated by reference herein in its entirety.

FIG. 11 shows an example of a humidifier tub with an open base or bottom. As illustrated, the tub 460 includes plastic molded sidewalls 464 and a heating apparatus 468 that cooperate to define a water chamber or compartment for water 462. The heating apparatus includes an overmolded protective coating 469, a thermally conductive hot plate 470 (e.g., metal hot plate), and a heating element 474 having heating tracks abutting against the hot plate 470. As illustrated, the heating apparatus is spaced upwardly from the lower ends of the sidewalls 464. The sidewalls may be overmolded onto the heating apparatus, without a bottom wall or bottom protective layer. Other materials with high thermal insulation may be used for the overmold. Also, an insulator or bottom wall (not shown) may be provided to the tub below the heating element 474.

FIG. 12-1 shows an example of a humidifier tub with a closed base or bottom. As illustrated, the tub 560 includes plastic molded sidewalls 564, a plastic molded bottom wall 566, and a heating apparatus 568 that cooperate to define a water chamber or compartment for water 562. The heating apparatus includes an overmolded protective coating 569, a thermally conductive hot plate 570 (e.g. metal hot plate), and a heating element 574 providing heating tracks. The sidewalls and bottom wall may be overmolded onto the heating apparatus.

In another example shown in FIG. 12-2, an inner portion of the tub 560 may be overmolded with thermally conductive plastics such that a hot plate 570 and heating element 574 are embedded in the overmold to form a heating apparatus 868. The overmold 861 includes a bottom wall 867 overmolded onto the bottom wall 566 of the tub and an intermediate wall 872 which covers the hot plate 570. The overmold 861 may also include sidewalls 863 overmolded onto the tub side walls 564. This arrangement may form a bio-compatible, cleanable, water/vapor sealed protection layer.

Figures 1, 15:
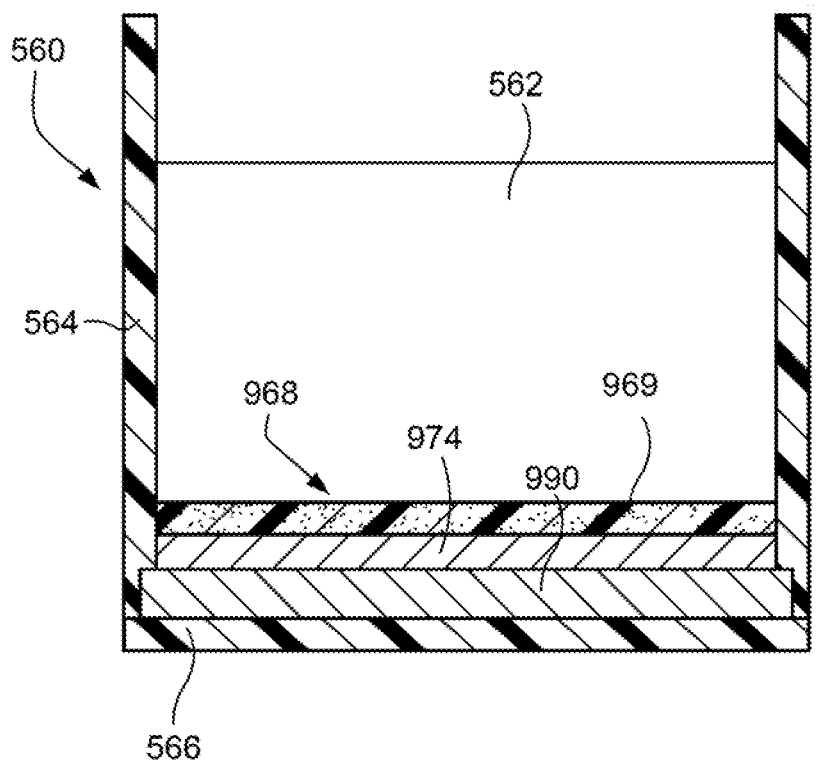
Figures 2, 15:
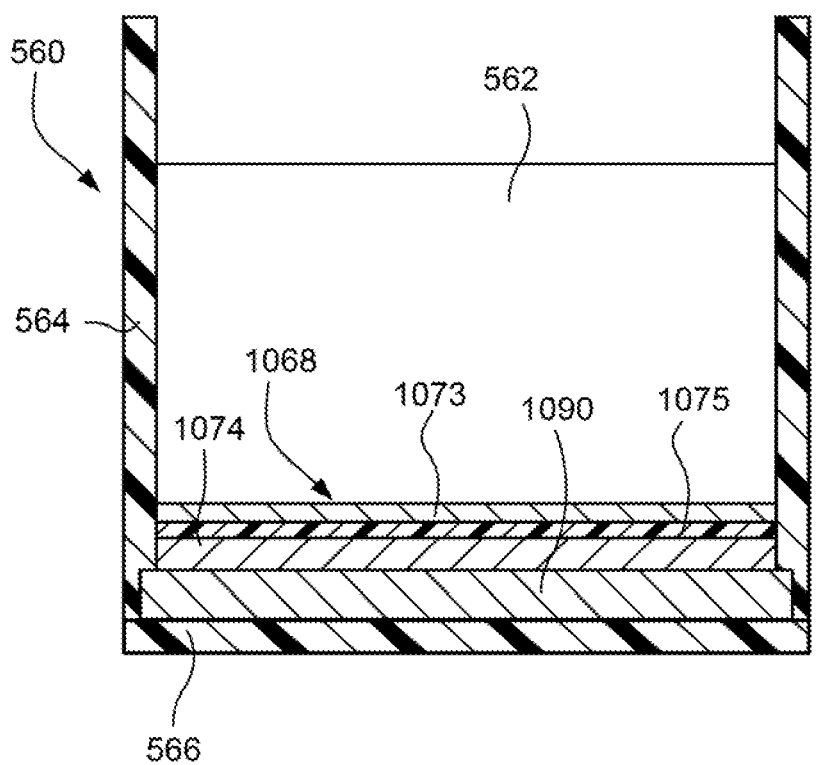

In an alternative arrangement of the heater assembly, the entire assembly may be formed in a different configuration such that a thermally conductive hot plate is no longer required, as shown in FIGS. 15-1 and 15-2. Referring to FIG. 15-1, a support substrate 990 is provided on the lower surface of the tub onto which the heating element 974 is bonded or applied in the same manner described above for applying the heating element 48 to the hot plate 44. In another example, the heater assembly may be assembled directly into a surface of a water tub, such as the bottom surface.

A thermally conductive protective coating 969, as described above, is overmolded over the heating element 974 to provide electrical insulation, corrosion resistance and/or damage protection. In this arrangement, the heating element 974 is positioned towards the water to be heated and the support substrate 990 is positioned relatively away from the water. The support substrate 990 serves primarily as a base for receiving the printed circuit and does not function as a heat sink or conductive means to heat the water. In this arrangement, the heater assembly is flipped upside down as compared to the embodiments described above using the metal hot plate such that heat transfer occurs in the opposite direction. The heating element 974 is essentially exposed to the water and consequently may provide improved thermal conductivity and thermal efficiency. Such an arrangement may also provide for more accurate or direct sensing of the temperature of the water.

The support substrate 990 may be formed of a lower cost PCB type material such as a composite epoxy material (CEM) of different grades (e.g., CEM3), a fiberglass reinforced epoxy laminate such as FR-4, or other such PCB type materials. The support substrate 990 may also be configured to provide thermal insulation to the outer surfaces of the tub.

In such arrangements the electrical connections are located on the internal surfaces of the tub. The electrical connections for thermal sensing or safety switches may be directly coupled to the heating element 974 prior to overmolding the heating element 974 within the tub.

As shown in FIG. 15-2, the protective coating or layer 1073 may include a thin layer of stainless steel that is applied over the heating element 1074. The stainless steel layer may be applied in any suitable manner that provides thermal contact between the stainless steel and the heating element. The thin layer of stainless steel may have a thickness of less than 1.2 mm (e.g., 0.05 to 1 mm). A thermally conductive laminate layer 1075 (e.g., Kapton™ film) may be provided between the protective coating 1073 and the heating element 1074 to provide electrical insulation. The thermally conductive laminate layer 1075 may also include a thermal adhesive (e.g., double sided adhesive) to attach the protective layer 1073.

The stainless steel layer may provide one or more of the following benefits: a protective cover to the heating element, anti-corrosion protection, and rigidity to the heater assembly (e.g., the stainless steel layer may form the heater assembly into a rigid structure).

In another example, the heating element 1074 may be formed without a thick support substrate 1090 such that the thin layer of stainless steel provides support to the flexible heater element while also providing a more compliant heater assembly that may be configured to conform to the shape of the water tub.

Electrical Connection

As noted above, the heating apparatus 68 may have exposed contact points (i.e., exposed contact pads 78) so that when the tub is placed on the bottom of the humidifier chamber, the contact points engage with counterpart contact points adapted to supply electrical power. In such example, the contact points within the humidifier chamber may be spring loaded, so that such contact points must be depressed to effect an electrical connection, e.g., contact points within the humidifier chamber engage only when the humidifier lid is closed to retain the humidifier tub within the humidifier chamber.

Figures 1, 8:
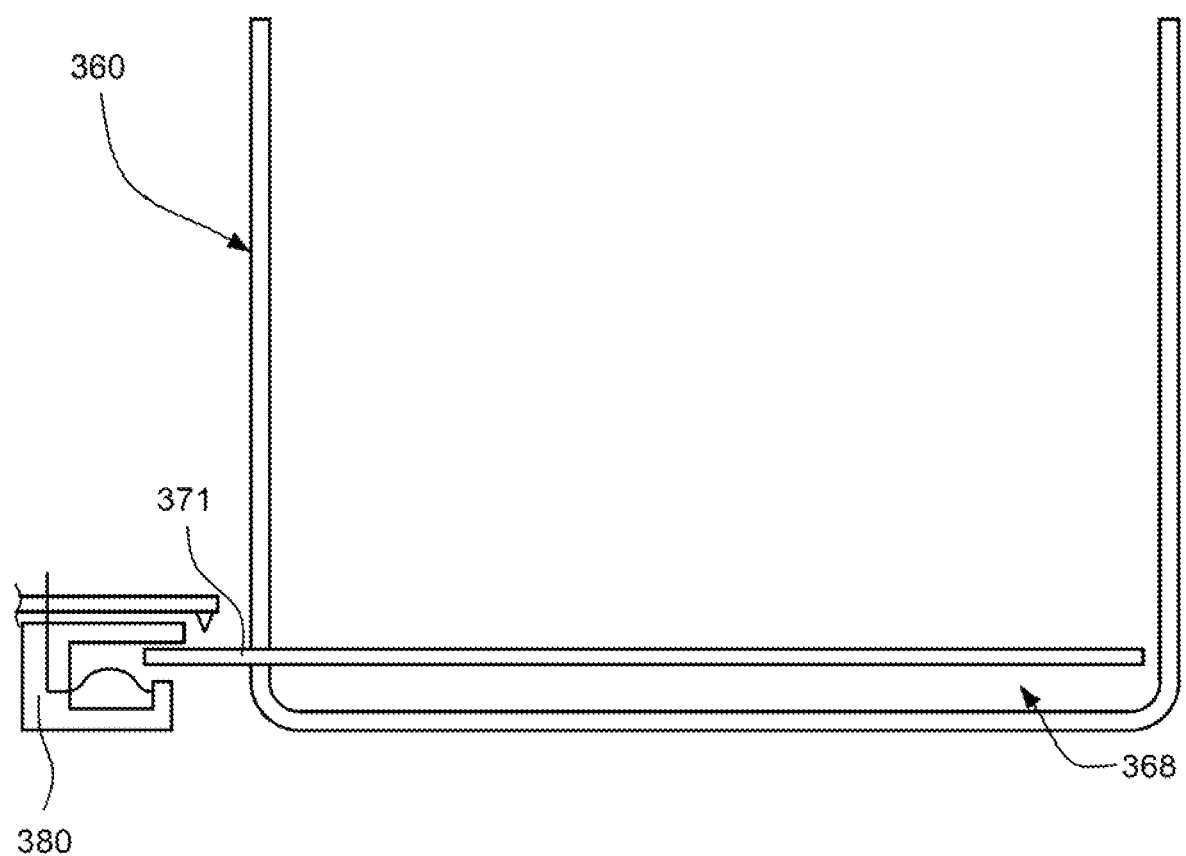
Figures 1, 9:
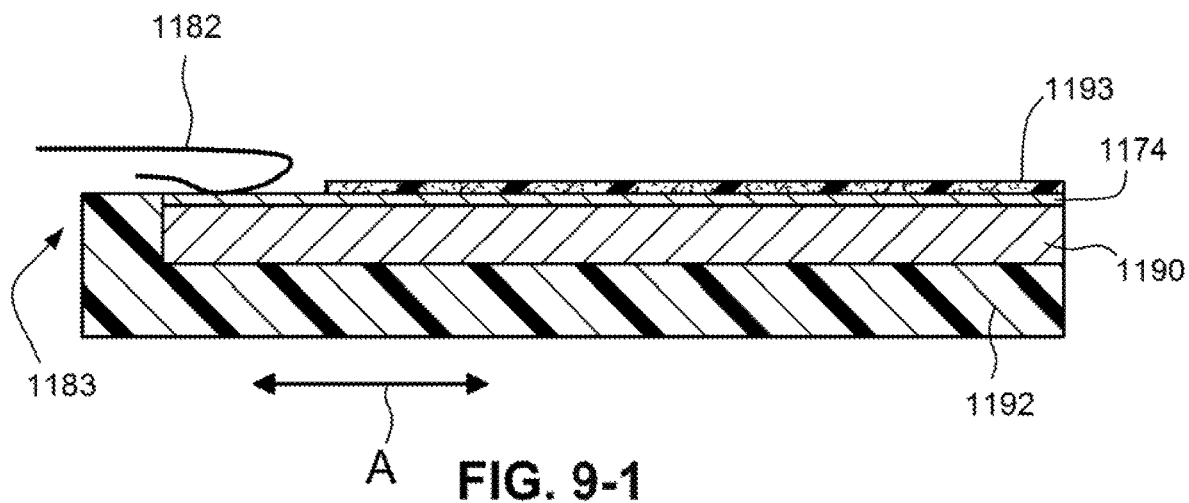
Figures 2, 9:
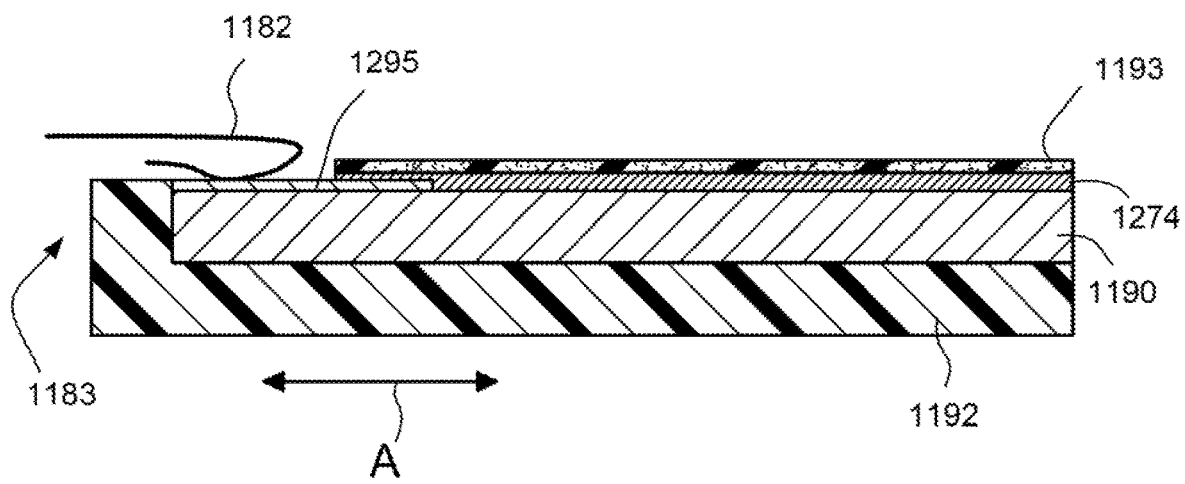
Figure 10:
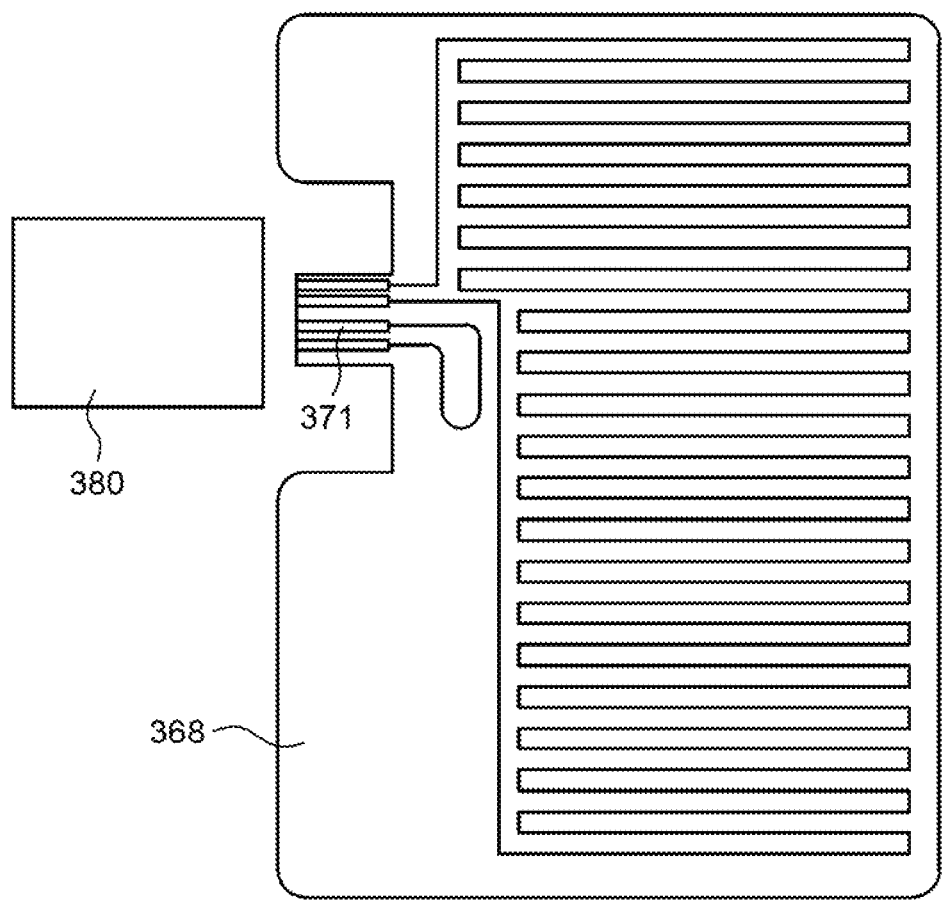
FIG. 10 is a schematic plan view of the heating apparatus and electrical contact structure shown in FIG. 8-1.

FIGS. 8 to 10 show another example of an electrical connection for a heating apparatus. In this example, the heating apparatus 368 integrated into the bottom of the humidifier tub 360 includes an exposed portion 371 adapted to engage an electrical contact structure 380 provided to the humidifier chamber when the tub is slid into an operative position within the humidifier chamber, i.e., slide-in type electrical connection.

As illustrated, the electrical contact structure 380 is in the form of a socket and includes a metallic spring arm 382 therewithin. In use, the exposed portion 371 of the heater apparatus engages the metallic spring arm 382 within the electrical contact structure 380 to effect an electrical connection. An advantage of this connection is that there is a "self cleaning" aspect which removes the build up of metal oxides on the connection points, since every slide-in/slide-out brushes one surface against another and wipes off any oxide build up.

Figure 14A:
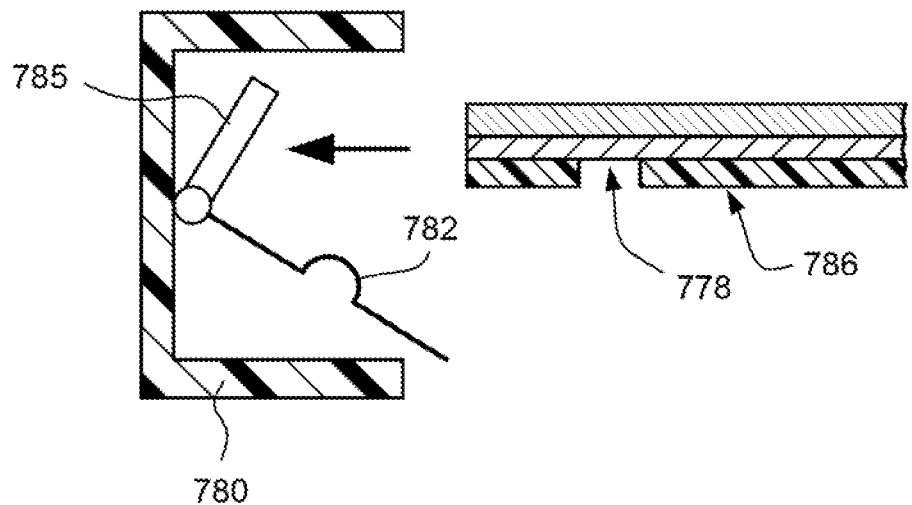
FIGS. 14A and 14B are schematic views of a heating apparatus and electrical contact structure according to an example of the present technology.
Figure 14B:
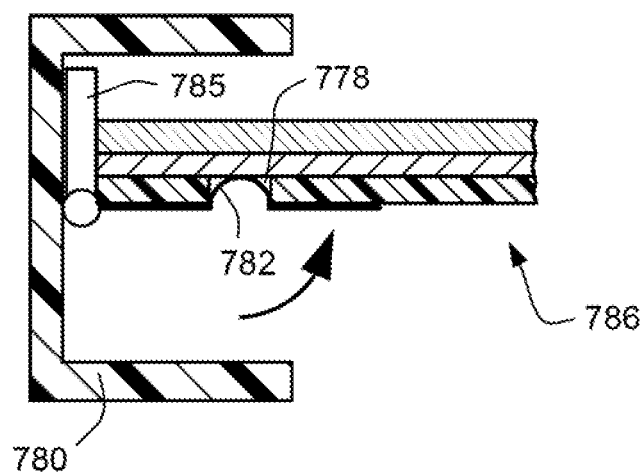

FIGS. 14A and 14B show another example of a slide-in type electrical connection for a heating apparatus. In this example, the metallic spring arm 782 is pivotally mounted within the electrical contact structure 780. In use, the end portion of the heating apparatus 786 may slide into the contact structure 780 and abut against stub 785 which will pivot and raise the spring arm 782 into electrical contact with an exposed contact pad 778 at the bottom of the heating apparatus, e.g., pivoting type slide-in connection. Such pivotal connection ensures that the spring arm 782 only contacts the exposed contact pad in use, i.e., spring arm avoids contact and potential wear of protective surfaces at the bottom of the heating apparatus.

As shown in FIG. 9-1, a protective contact edge 1183 may be formed in a connector region by overmolding an additional outer protective coating 1192 around at least a portion of the heater assembly. Referring to FIG. 9-1, a heater assembly includes a support substrate 1190, a heating element 1174 (e.g., a copper layer), an overmolded protective coating 1193 on top of the heating element 1174, and the outer protective coating 1192 overmolded to a bottom surface of the support substrate 1190 and around an outer edge of the heater assembly to provide a protective coating along an edge of the connector region of the heater assembly. The heating element may be exposed from the outer protective coating 1192 in the connector region to provide a contact portion for an electrical contact arm 1182. The contact portion may be provided with a layer of Nickel (e.g., 20 to 80 μm) and a layer of Gold (e.g., 20 to 50 μm) over the Nickel to protect this area. The outer protective coating 1192 may provide a rigid or semi-rigid support to the heater assembly. The outer protective coating 1192 may also protect the electrical connection from water egress.

Temperature Sensing

Temperature sensing of the heating apparatus may be provided for fault mitigation and temperature feedback control. For example, the temperature of the heating apparatus or water may be determined, and then power may be cut off to the heating element if the temperature is too high. For temperature feedback, the temperature of the heating apparatus or water may be determined to better control the powering profile and coordinate the required level of vaporization/humidification.

The temperature of the heating apparatus or water may be determined in alternative manners. Alternative examples of sensors for determining temperature of the heating apparatus are described below.

Non-Contact Sensor

A non-contact type sensor may be provided to determine the temperature of the heating apparatus. Such non-contact type sensor is spaced from the heating surface or heating tracks of the heating apparatus.

Figures 1A, 8:
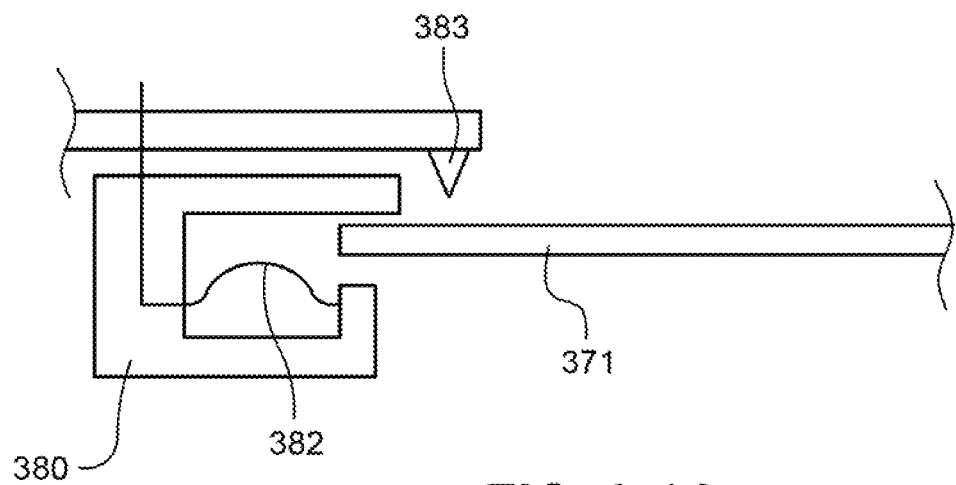

In an example, an infrared (IR) sensor may be located near the heating surface of the heating apparatus and sense the radiation (heat) given off the heating apparatus to determine the temperature of the heating apparatus. An example of such arrangement is shown in FIG. 8-1A which shows an IR sensor 383 near the heating surface of the exposed portion 371 of the heating apparatus.

In another example, a convection sensor may be located near the heating surface of the heating apparatus (e.g., similarly positioned to the sensor shown in FIG. 8-1A) and sense the temperature of the air in the gap between the convection sensor and the heating apparatus to determine the temperature of the heating apparatus.

Contact Sensor

A contact type sensor may be provided to determine the temperature of the heating apparatus. Such contact type sensor is in contact with the heating surface or heating tracks of the heating apparatus.

In an example, the sensor may include a thermo-resistive material in which material resistance changes as the temperature varies. By measuring the resistance change, the temperature may be determined.

In another example, the sensor may include a thermo-magnet switch in which the magnetic field strength changes with the change of temperature. By measuring the magnetic field strength change, the temperature may be determined.

In another example, the sensor may include a bi-metal strip material in which the shape or springiness of the metal changes with the temperature. By measuring the shape or springiness change, the temperature may be determined. An exemplary advantage of this example is that the strip material may disconnect at a particular temperature, thus providing a thermo fuse for the system. Such off-heater sensor arrangements may also be a combined sensor and manual resettable switch.

On-Board Temperature Sensing and Thermo Fuse

In an example, as shown in FIG. 5 and noted above, a thermo sensor 52A may be provided to the heating element to measure the temperature of the heating tracks and a thermo fuse 52B may be provided to stop current flow through the heating element if the heat becomes excessive. The heating track itself may also be a temperature sensor.

Temperature Sensing Ability

In the present technology, the heating apparatus may be formed using known PCB manufacturing techniques for making metal PCBs, such as MCPCB techniques. Such heating apparatus according to the present technology provides a heating profile that is substantially evenly distributed across the heater apparatus. For example, temperature differences (ΔT) across the hot plate during heating up is much lower (indicates much higher thermal conductivity and fast heat transfer), low thermal stress on hot plate and surrounded material temperature ramp up and operation, low thermal/mechanical stress on hot plate and surrounded material during temperature ramp up and operation, low back side temperature which will not heat up the casing bottom.

The temperature transfer from the heating tracks to the metal hot plate is efficient and therefore the temperature of the surface of the hot plate is likely to be similar to that of the heating track (low thermal gradient/heat sink). As track resistance varies with respect to track temperature, a current (I) and voltage (V) circuitry measurement may be used to calculate the resistance (R) of the tracks [R=V/I], and knowing the R vs. T profile, the temperature of the hot plate may be determined by just determining the R. In this way, a separate NTC (negative thermal coefficient) thermistor componentry may not be needed to sense temperature. Such conversion circuit may also be used for fault detection and protection, such as heater over temperature, open circuit, or poor connection or shorting.

Temperature Limiting/Overheating Protection

In an example, the heating apparatus according to the present technology may provide a heating surface temperature that can only reach a maximum temperature for a chosen input power. This is due to efficient heat transfer from the heating track to the heating surface, effective heat dissipation from the heating surface, and copper heating tracks reaching a limit temperature with a given power input. Given this, a thermo fuse (to mitigate against overheating) may possibly be removed as the heating apparatus would have over-heating self protection capability. Removal of the thermo fuse may provide savings in componentry and assembly costs.

In a further example shown in FIG. 9-2, the heating tracks may be formed from polymer thick film (PTF) 1274 in combination with copper conductors (e.g., heating tracks) 1295 that are printed on a hot plate (e.g., the hot plate 44 described in the examples above) or a support substrate 1190. The copper conductor 1295 and the PTF 1274 are provided in appropriate quantities to provide variation in heating across the heating element. The PTF 1274 may comprise a positive temperature coefficient (PTC) to provide a sensing and thermal protection function. The copper conductor 1295 forms a contact portion and act as conductors for electricity from an electrical contact arm 1182 and the PTF 1274 as the heater. The contact portion may be provided with a layer of Nickel (e.g., 20 to 80 µm) and a layer of Gold (e.g., 20 to 50 µm) over the Nickel to protect this area. The heater may also be formed by the copper tracks 1295 in combination with the PTF 1274 to achieve the required heating and protection properties. In an example, one or more sections of PTF 1274 may be provided in series with the copper tracks 1295 to form a thermal fuse.

In an exemplary manufacturing step, the heating apparatus may be enclosed or otherwise covered in stainless steel which provides the advantage of protecting the heating apparatus from corrosion. This process may be used as an alternative, or in conjunction with the step of anodizing the hot plate. The result of this manufacturing step would be a heating apparatus that is enclosed or otherwise covered in stainless steel. As an alternative to stainless steel, another thermally conductive material that resists scratching, and resists corrosion, such as hard anodized stamped aluminium may be used to enclose or cover.

The present technology is particularly useful in a lower temperature heating application, e.g., less than 100 C, or less than 80 C, or less than 70 C. Furthermore the power output may be less than about 5 W/cm2, or less than about 2 W/cm2, or less than about 1 W/cm2, for example around 0.6 W/cm2. A higher temperature application may require a power output of around 60 W/cm2. Furthermore the present technology facilitates the use of lower cost materials and lower cost processes than may be required for a higher temperature application. For example, in the present technology, the manufacturing process of etching may be used instead of printing thermally conductive inks. The etching process may give rise to a more accurate heating track than the printing process. Furthermore, the present technology allows the use of a cheaper dielectric material, such as an organic material whereas a high temperature process and application requires an inorganic dielectric and concomitant higher material and process costs. Furthermore the present technology allows the use of a lower cost hot plate, for example one made of aluminium or another lower cost material.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A humidifier, comprising:
   a tub adapted to hold a liquid; and
   a heating apparatus comprising:
     a heating element which converts electrical power to heat energy;
     a thermally conductive substrate layer, the thermally conductive substrate layer having a first surface and a second surface;
     a dielectric laminate layer between the heating element and the first surface of the thermally conductive substrate layer, wherein the dielectric laminate layer is thermally conductive to transfer heat energy from the heating element to the thermally conductive substrate layer, and wherein the second surface of the thermally conductive substrate layer is configured to heat the liquid in the tub; and
     a protective layer covering an outer surface of the heating element,
     wherein the protective layer extends over a peripheral edge of the heating element and onto portions of the dielectric laminate layer.

2. A humidifier according to claim 1, wherein the thermally conductive substrate layer is constructed of a metal or metal alloy.

3. A humidifier according to claim 2, wherein the metal or metal alloy includes at least one of aluminium, stainless steel or copper.

4. A humidifier according to claim 1, wherein the dielectric laminate layer is constructed of a ceramic material, a polymeric material, or a ceramic and polymeric mixture material.

5. A humidifier according to claim 1, wherein said heating element comprises a heating track etched in a copper or alloy or Positive Temperature Coefficient (PTC) layer.

6. A humidifier according to claim 5, wherein the heating track is associated with contact pads for electrical leads and at least one electrical component.

7. A humidifier according to claim 5, wherein the heating track includes a width in a range of about 0.4 mm to 2 mm.

8. A humidifier according to claim 5, wherein a temperature of the heating apparatus is determined by determining a resistance of the heating track.

9. A humidifier according to claim 5, wherein the protective layer is printed onto at least the copper or alloy or PTC layer.

10. A humidifier according to claim 9, wherein the protective layer is printed onto at least the heating track.

11. A humidifier according to claim 9, wherein the protective layer extends over a peripheral edge of the dielectric laminate layer and onto a peripheral portion of the first surface of the thermally conductive substrate layer.

12. A humidifier according to claim 9, wherein the protective layer includes a solder mask.

13. A humidifier according to claim 1, wherein the heating apparatus provides a heating surface temperature that can only reach a maximum temperature for a chosen input power.

14. A humidifier according to claim 1, wherein the heating apparatus is provided to a humidifier chamber adapted to receive the tub.

15. A humidifier according to claim 1, wherein the heating apparatus is integral with the tub.

16. A humidifier according to claim 1, wherein the heating apparatus is assembled using an automated assembly process.

17. A respiratory apparatus for delivering breathable gas to a patient, comprising:
 a flow generator to generate a supply of breathable gas to be delivered to the patient; and
 the humidifier of claim 1, the humidifier being configured to vaporize water and deliver water vapor to humidify the supply of breathable gas.

* * * * *